United States Patent
Fuchiwaki

(10) Patent No.: US 10,787,467 B2
(45) Date of Patent: Sep. 29, 2020

(54) POLYCYCLIC COMPOUND AND ORGANIC ELECTROLUMINESCENCE DEVICE INCLUDING THE SAME

(71) Applicant: SAMSUNG DISPLAY CO., LTD., Yongin-si, Gyeonggi-do (KR)

(72) Inventor: Junta Fuchiwaki, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 399 days.

(21) Appl. No.: 15/813,677

(22) Filed: Nov. 15, 2017

(65) Prior Publication Data

US 2018/0148462 A1 May 31, 2018

(30) Foreign Application Priority Data

Nov. 30, 2016 (KR) .......................... 10-2016-0162144

(51) Int. Cl.
| | | |
|---|---|---|
| C07F 7/30 | (2006.01) | |
| C07F 7/10 | (2006.01) | |
| C07D 471/10 | (2006.01) | |
| C07D 471/22 | (2006.01) | |
| C07D 471/20 | (2006.01) | |
| C07D 498/22 | (2006.01) | |
| C09K 11/06 | (2006.01) | |
| H01L 51/50 | (2006.01) | |
| H01L 51/00 | (2006.01) | |
| C07D 498/20 | (2006.01) | |
| C07F 7/08 | (2006.01) | |

(52) U.S. Cl.
CPC .............. *C07F 7/30* (2013.01); *C07D 471/10* (2013.01); *C07D 471/20* (2013.01); *C07D 471/22* (2013.01); *C07D 498/20* (2013.01); *C07D 498/22* (2013.01); *C07F 7/0816* (2013.01); *C07F 7/10* (2013.01); *C09K 11/06* (2013.01); *H01L 51/0072* (2013.01); *H01L 51/0094* (2013.01); *H01L 51/5056* (2013.01); *C09K 2211/1096* (2013.01); *H01L 51/5096* (2013.01); *H01L 2227/323* (2013.01)

(58) Field of Classification Search
CPC .. C07D 471/10; C07D 471/20; C07D 471/22; C07D 498/20; C07D 498/22; C07F 7/0816; C07F 7/10; C07F 7/30; C09K 11/06; C09K 2211/1096; H01L 2227/323; H01L 51/0072; H01L 51/0094; H01L 51/5056; H01L 51/5096
See application file for complete search history.

(56) References Cited

U.S. PATENT DOCUMENTS

| | | | | |
|---|---|---|---|---|
| 7,714,149 B2 * | 5/2010 | Zhang | .................. | C07C 231/18 549/220 |
| 8,632,893 B2 | 1/2014 | Lin et al. | | |
| 10,224,488 B2 * | 3/2019 | Yen | ...................... | H01L 51/0071 |
| 10,505,128 B2 * | 12/2019 | Chung | ................ | H01L 51/0072 |
| 2010/0171417 A1 | 7/2010 | Kitamra et al. | | |
| 2015/0188056 A1 | 7/2015 | Suda | | |
| 2016/0093812 A1 * | 3/2016 | Stoessel | ................. | C09K 11/06 257/40 |
| 2016/0172600 A1 | 6/2016 | MacDonald et al. | | |
| 2016/0372681 A1 * | 12/2016 | Parham | ............... | H01L 51/0061 |
| 2017/0125701 A1 * | 5/2017 | Pfister | .................. | C09K 11/025 |
| 2018/0205019 A1 * | 7/2018 | Fuchiwaki | .......... | H01L 51/0059 |

FOREIGN PATENT DOCUMENTS

| | | | |
|---|---|---|---|
| JP | 2002-265938 A | | 9/2002 |
| JP | 2003-243178 A | * | 8/2003 |
| JP | 2004-253298 A | * | 9/2004 |
| KR | 10-0679724 B1 | | 1/2007 |
| KR | 10-2011-0120075 A | | 11/2011 |
| KR | 10-2015-0033700 A | | 4/2015 |
| KR | 10-2015-0143552 A | | 12/2015 |
| KR | 10-2016-0035062 A | | 3/2016 |
| KR | 10-2017-0124012 | * | 11/2017 |
| WO | WO 2007/110228 A1 | | 10/2007 |
| WO | WO 2013/083216 A1 | * | 6/2013 |
| WO | WO 2014/002629 A1 | | 5/2016 |

OTHER PUBLICATIONS

Machine translation for KR 20110120075 A (publication dated Nov. 3, 2011). (Year: 2011).*
Machine translation for KR 10-2017-0124012 (publication dated Nov. 9, 2017). (Year: 2017).*
Lin, Chi-Jen, et al.; High Energy Gap OLED Host Materials for Green and Blue PHOLED Materials, Journal of Display Technology, vol. 5, No. 6, Jun. 2009, pp. 236-240.

* cited by examiner

*Primary Examiner* — Dawn L Garrett

(74) *Attorney, Agent, or Firm* — Lewis Roca Rothgerber Christie LLP

(57) ABSTRACT

A polycyclic compound and an organic electroluminescence device, the polycyclic compound being represented by Formula 1:

[Formula 1]

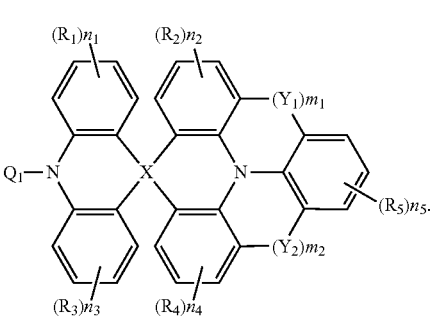

19 Claims, 2 Drawing Sheets

POLYCYCLIC COMPOUND AND ORGANIC ELECTROLUMINESCENCE DEVICE INCLUDING THE SAME

CROSS-REFERENCE TO RELATED APPLICATIONS

Korean Patent Application No. 10-2016-0162144, filed on Nov. 30, 2016, in the Korean Intellectual Property Office, and entitled: "Polycyclic Compound and Organic Electroluminescence Device Including the Same," is incorporated by reference herein in its entirety.

BACKGROUND

1. Field

Embodiments relate to a polycyclic compound and an organic electroluminescence device including the same.

2. Description of the Related Art

Development on an organic electroluminescence display as an image display is being actively conducted. An organic electroluminescence display is different from a liquid crystal display and is a self-luminescent display which accomplishes display by recombining holes and electrons injected from a first electrode and a second electrode in an emission layer and emitting light from a luminescent material which is an organic compound included in the emission layer.

As an organic electroluminescence device, for example, an organic device composed of a first electrode, a hole transport layer disposed on the first electrode, an emission layer disposed on the hole transport layer, an electron transport layer disposed on the emission layer, and a second electrode disposed on the electron transport layer is known. Holes are injected from the first electrode, and the injected holes move via the hole transport layer to be injected into the emission layer. Meanwhile, electrons are injected from the second electrode, and the injected electrons move via the electron transport layer to be injected into the emission layer. By recombining the holes and electrons injected into the emission layer, excitons are generated in the emission layer. The organic electroluminescence device emits light using light emitted during the transition of the excitons back to a ground state. In addition, the configuration of an organic electroluminescence device is not limited to those described above, and various modifications may be possible.

SUMMARY

Embodiments are directed to a polycyclic compound and an organic electroluminescence device including the same.

The embodiments may be realized by providing a polycyclic compound represented by the following Formula 1:

[Formula 1]

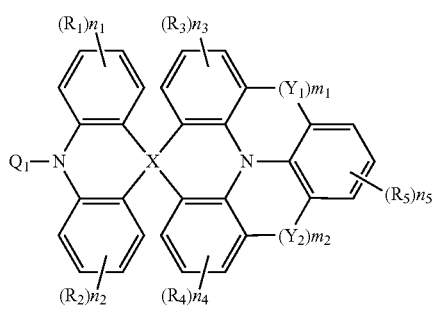

wherein, in Formula 1, X is C, Si, Ge, or Sn, $Y_1$ and $Y_2$ are each independently O, S, $CR_6R_7$, $SiR_8R_9$, $GeR_{10}R_{11}$, or $SnR_{12}R_{13}$, $R_1$ to $R_{13}$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group, $R_1$ to $R_{13}$ are separate or form a ring by combining adjacent groups with each other, $Q_1$ is a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $n_1$ and $n_2$ are each independently an integer of 0 to 4, $n_3$ to $n_5$ are each independently an integer of 0 to 3, $m_1$ and $m_2$ are each independently 0 or 1, and when X is C or Si, at least one of $m_1$ or $m_2$ is 1.

$Y_1$ and $Y_2$ may each independently be represented by the following Formula 2:

[Formula 2]

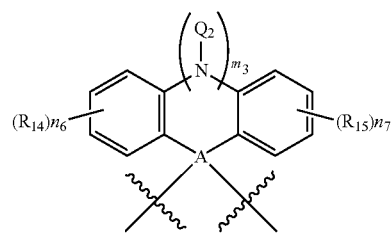

wherein, in Formula 2, A may be C, Si, Ge, or Sn, $R_{14}$ and $R_{15}$ may each independently be a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group, $R_{14}$ and $R_{15}$ may be separate or form a ring by combining adjacent groups with each other, $Q_2$ may be a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $n_6$ and $n_7$ may each independently be an integer of 0 to 4, $m_3$ may be 0 or 1, and

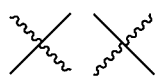

represent bonding sites of $Y_1$ and $Y_2$ in Formula 1.

The polycyclic compound represented by Formula 1 may be represented by any one of the following Formulae 3-1 to 3-6:

[Formula 3-1]

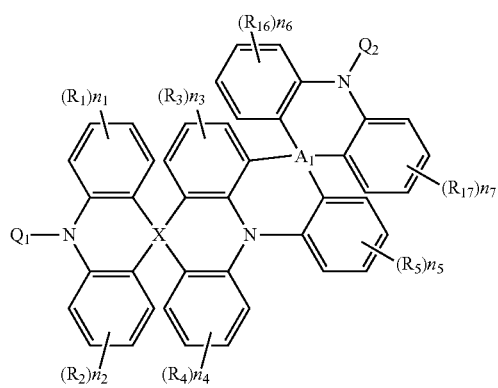

[Formula 3-2]

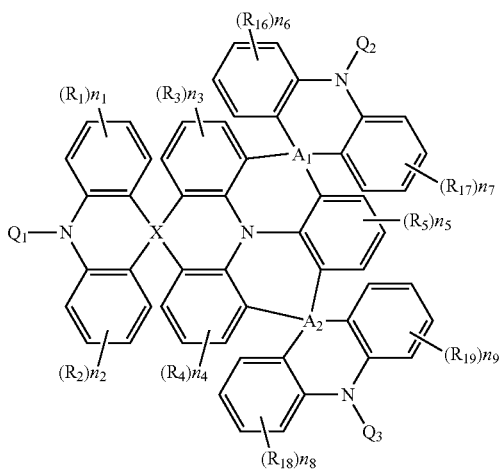

[Formula 3-3]

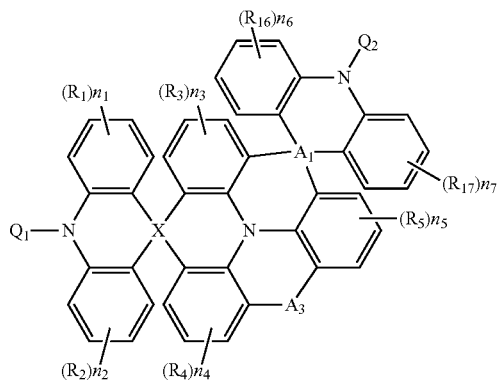

[Formula 3-4]

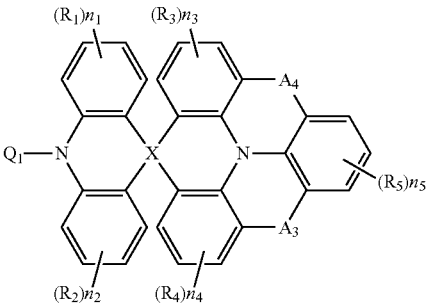

[Formula 3-5]

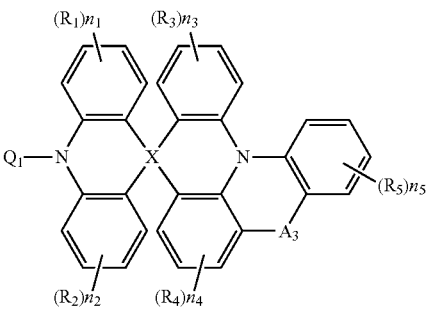

[Formula 3-6]

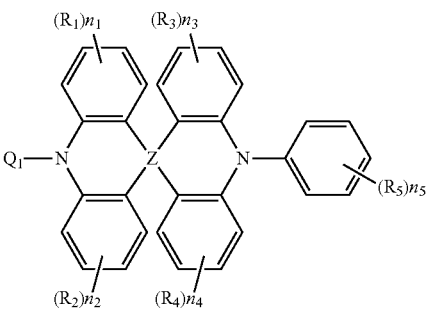

wherein, in Formulae 3-1 to 3-6. $A_1$ and $A_2$ may each independently be C, Si, Ge, or Sn, $A_3$ and $A_4$ may each independently be O, S, $CR_{20}R_{21}$, $SiR_{22}R_{23}$, $GeR_{24}R_{25}$, or $SnR_{26}R_{27}$, $R_{16}$ to $R_{27}$ may each independently be a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group, $R_{16}$ to $R_{27}$ may be separate or form a ring by combining adjacent groups with each other, $Q_2$ and $Q_3$ may each independently be a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, Z may be Ge or Sn, $n_6$ to $n_9$ may each independently be an integer of 0 to 4, and X, $Q_1$, $R_1$ to $R_5$, and $n_1$ to $n_5$ may be defined the same as those of Formula 1.

$R_{20}$ to $R_{27}$ may each independently be a hydrogen atom, a substituted or unsubstituted alkyl group having 1 to 10 carbon atoms, or a substituted or unsubstituted aryl group having 6 to 15 ring carbon atoms.

$Q_1$ to $Q_3$ may each independently be a substituted or unsubstituted alkyl group having 1 to 10 carbon atoms or a substituted or unsubstituted aryl group having 6 to 15 ring carbon atoms.

X may be C, Si, or Ge.

$Y_1$ and $Y_2$ may each independently be $CR_6R_7$ or $SiR_8R_9$.

The polycyclic compound represented by Formula 1 may be a compound of the following Compound Group 1:

[Compound Group 1]

1

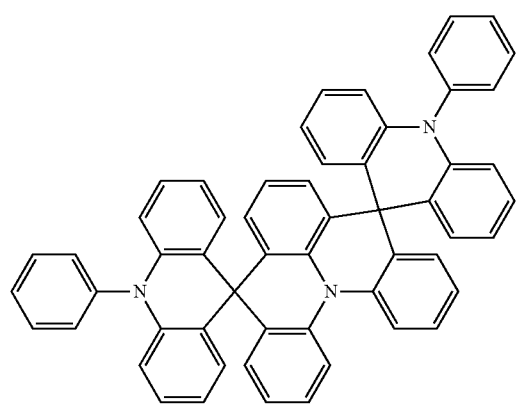

2

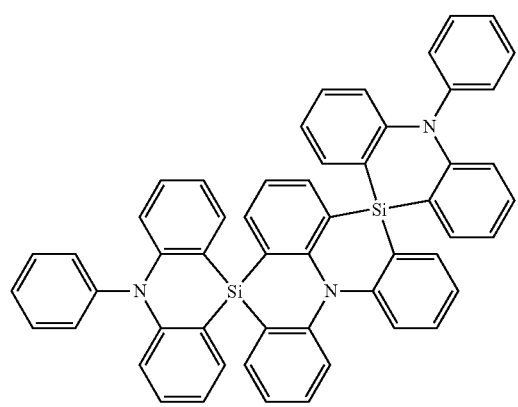

3

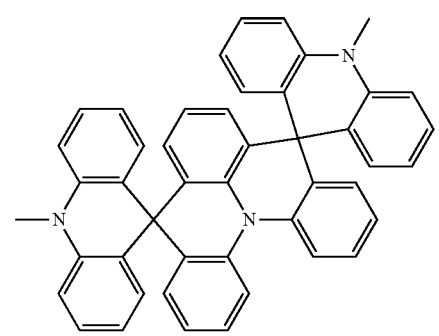

-continued

4

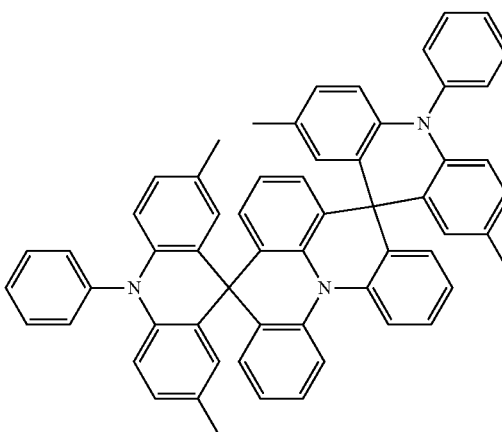

5

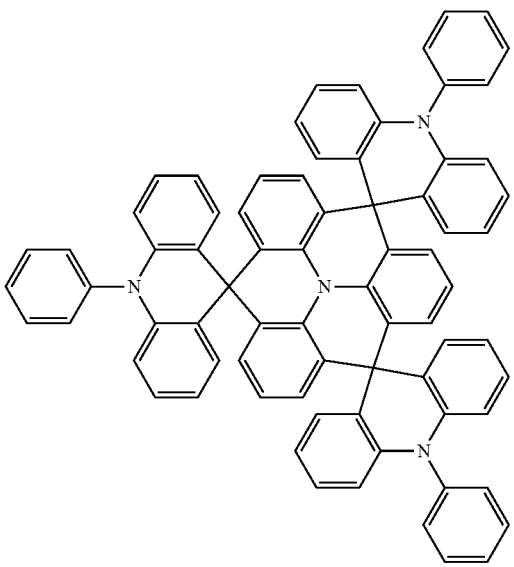

6

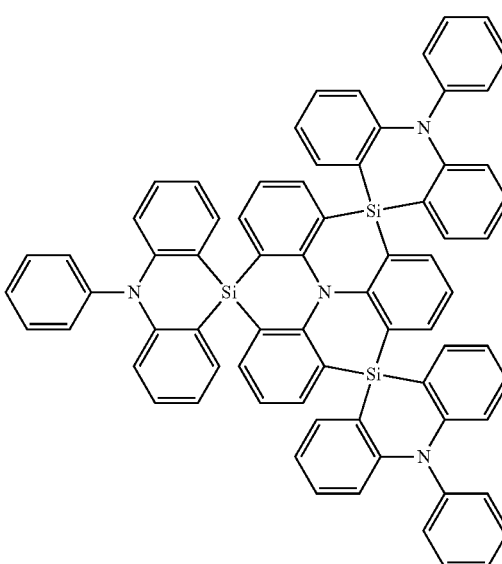

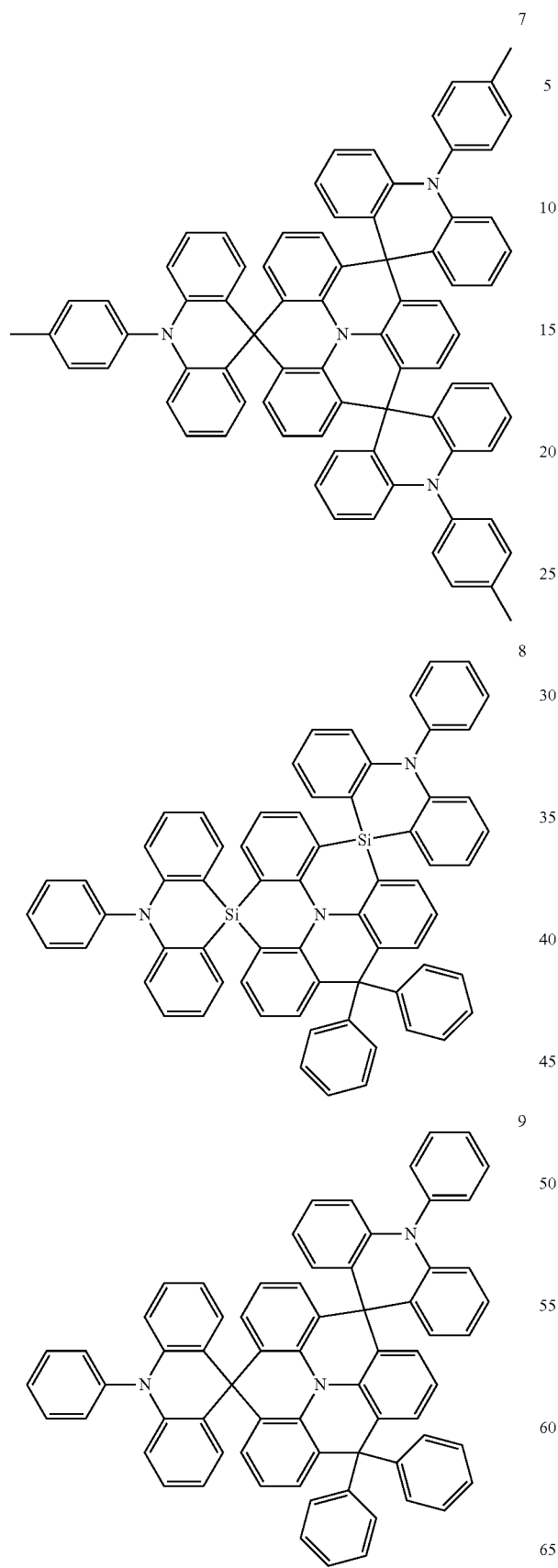
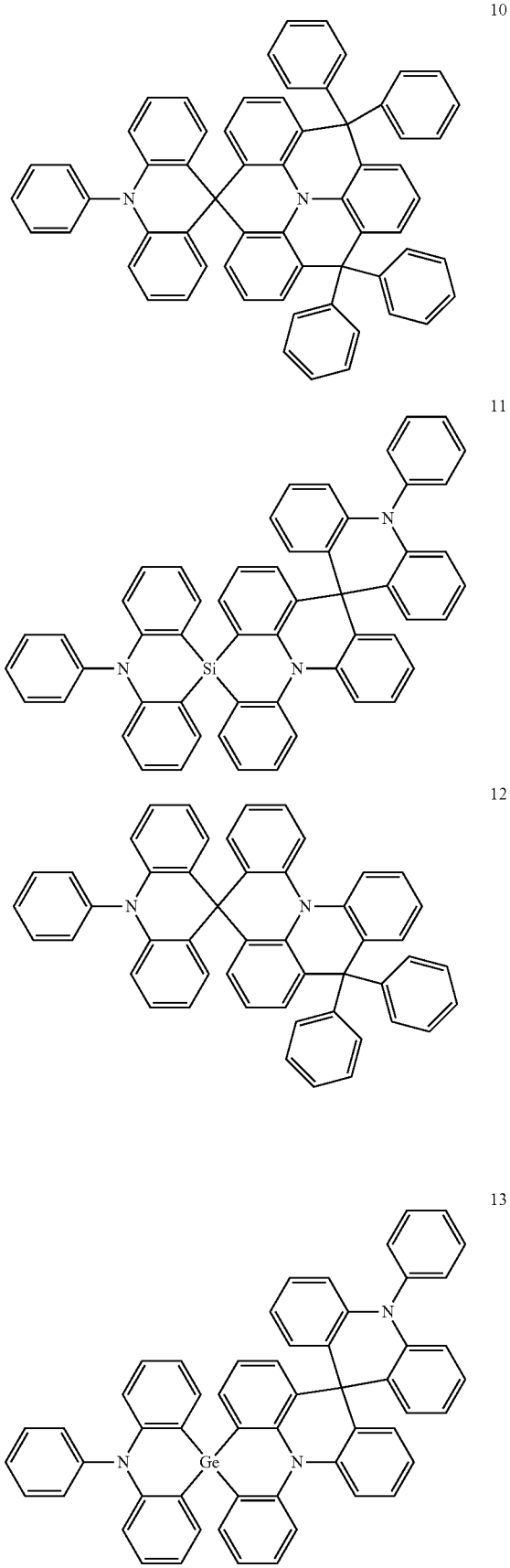

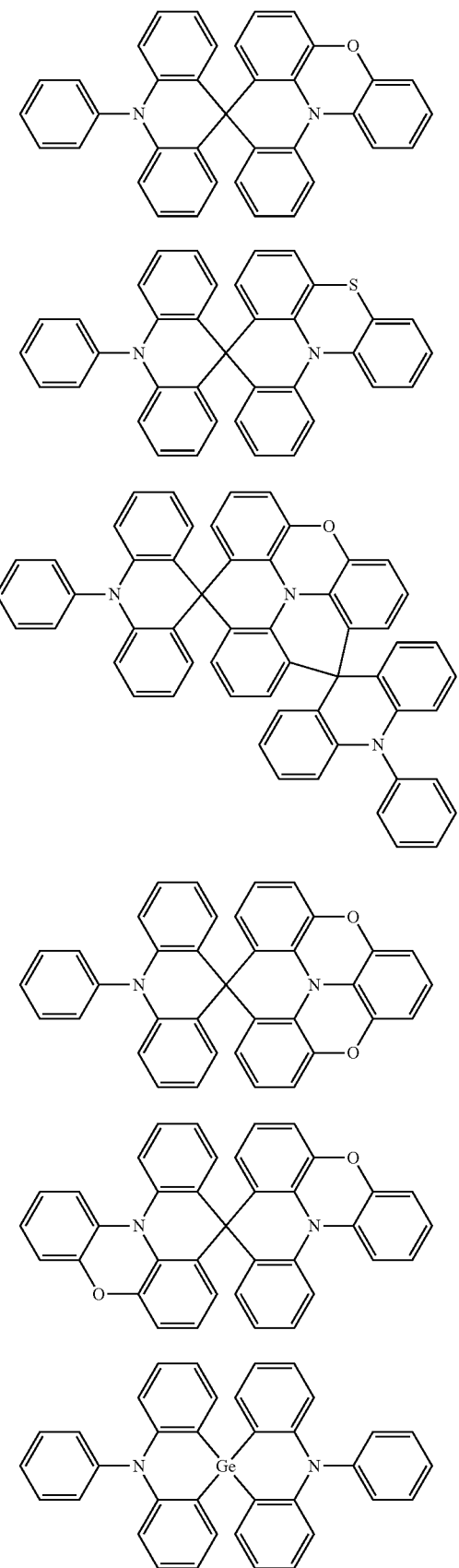

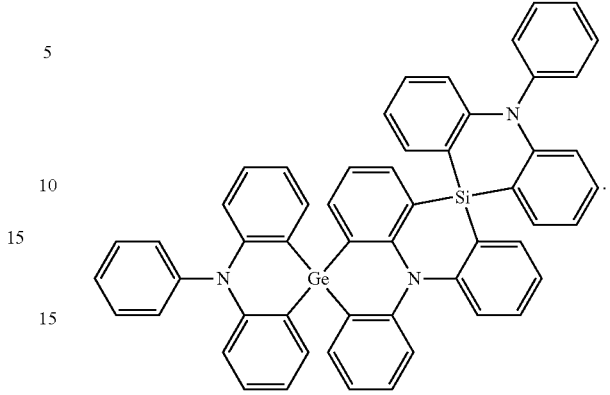

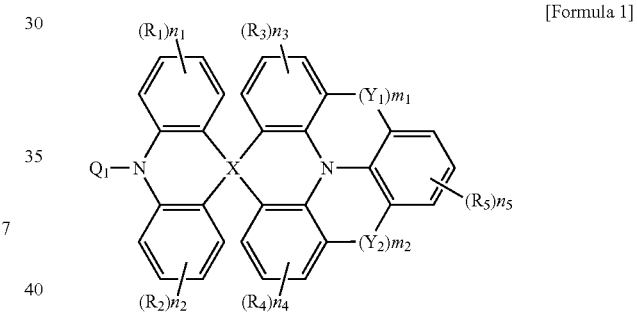

The embodiments may be realized by providing an organic electroluminescence device including a first electrode; a hole transport region on the first electrode; an emission layer on the hole transport region; an electron transport region on the emission layer; and a second electrode on the electron transport region, wherein the hole transport region includes a polycyclic compound represented by the following Formula 1:

[Formula 1]

$$Q_1-N\begin{array}{c}(R_1)n_1 \quad (R_3)n_3\\ \\ X\\ \\ (R_2)n_2 \quad (R_4)n_4\end{array}N\begin{array}{c}(Y_1)m_1\\ \\ (R_5)n_5\\ \\ (Y_2)m_2\end{array}$$

wherein, in Formula 1, X is C, Si, Ge, or Sn, $Y_1$ and $Y_2$ are each independently O, S, $CR_6R_7$, $SiR_8R_9$, $GeR_{10}R_{11}$, or $SnR_{12}R_{13}$, $R_1$ to $R_{13}$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group, $R_1$ to $R_{13}$ are separate or form a ring by combining adjacent groups with each other. $Q_1$ is a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $n_1$ and $n_2$ are each independently an integer of 0 to 4, $n_3$ to $n_5$ are each independently an integer of 0 to 3, $m_1$ and $m_2$ are each independently 0 or 1, and when X is C or Si, at least one of $m_1$ or $m_2$ is 1.

The hole transport region may include a hole injection layer on the first electrode; and a hole transport layer on the hole injection layer, and the hole transport layer may include the polycyclic compound represented by Formula 1.

The hole transport region may include a hole injection layer on the first electrode; a hole transport layer on the hole injection layer; and an electron blocking layer on the hole transport layer, and the electron blocking layer may include the polycyclic compound represented by Formula 1.

$Y_1$ and $Y_2$ may each independently be represented by the following Formula 2:

[Formula 2]

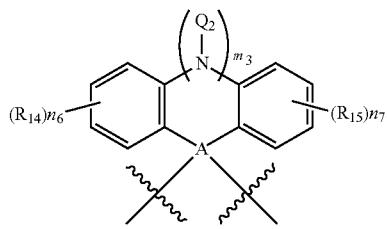

wherein, in Formula 2, A may be C, Si, Ge, or Sn, $R_{14}$ and $R_{15}$ may each independently be a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group, $R_{14}$ and $R_{15}$ may be separate or form a ring by combining adjacent groups with each other, $Q_2$ may be a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $n_6$ and $n_7$ may each independently be an integer of 0 to 4, $m_3$ may be 0 or 1, and

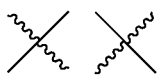

represent bonding sites of $Y_1$ and $Y_2$ in Formula 1.

The polycyclic compound represented by Formula 1 may be represented by any one of the following Formulae 3-1 to 3-6:

[Formula 3-1]

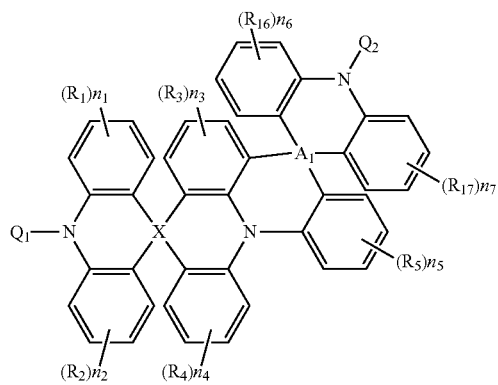

[Formula 3-2]

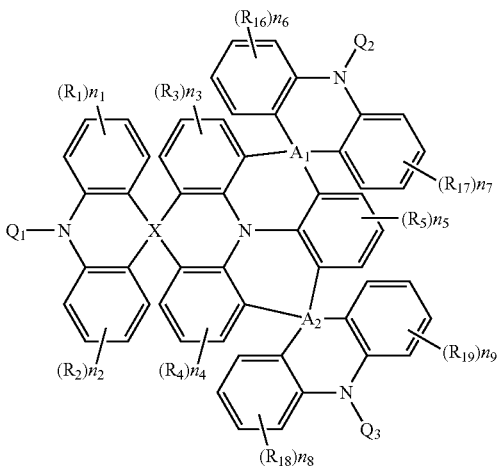

[Formula 3-3]

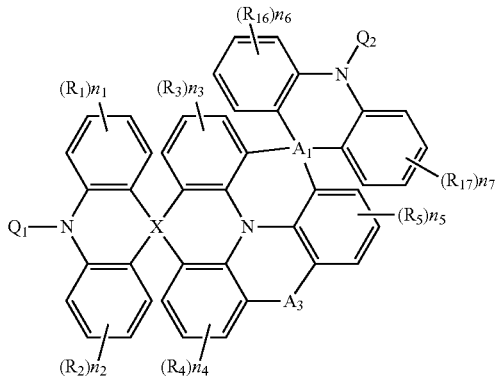

[Formula 3-4]

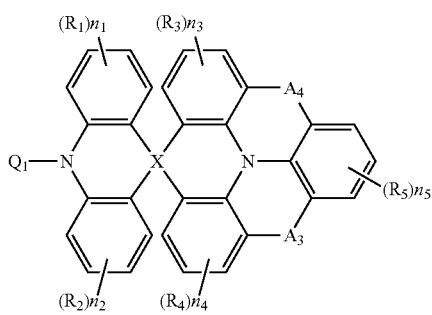

-continued

[Formula 3-5]

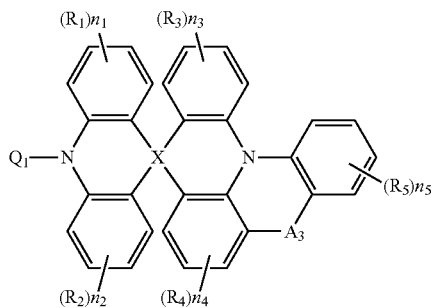

[Formula 3-6]

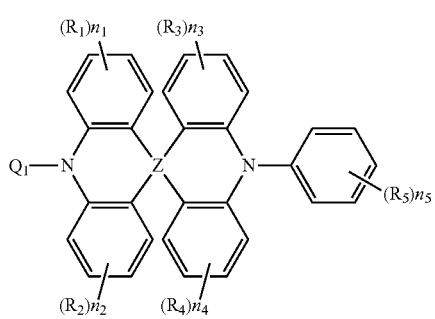

wherein, in Formulae 3-1 to 3-6, $A_1$ and $A_2$ may each independently be C, Si, Ge, or Sn, $A_3$ and $A_4$ may each independently be O, S, $CR_{20}R_{21}$, $SiR_{22}R_{23}$, $GeR_{24}R_{25}$, or $SnR_{26}R_{27}$, $R_{16}$ to $R_{27}$ may each independently be a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group, $R_{16}$ to $R_{27}$ may be separate or form a ring by combining adjacent groups with each other, $Q_2$ and $Q_3$ may each independently be a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, Z may be Ge or Sn, $n_6$ to $n_9$ may each independently be an integer of 0 to 4, and X, $Q_1$, $R_1$ to $R_5$, and $n_1$ to $n_5$ may be defined the same as those of Formula 1.

$R_{20}$ to $R_{27}$ may each independently be a hydrogen atom, a substituted or unsubstituted alkyl group having 1 to 10 carbon atoms, or a substituted or unsubstituted aryl group having 6 to 15 ring carbon atoms.

$Q_1$ to $Q_3$ may each independently be a substituted or unsubstituted alkyl group having 1 to 10 carbon atoms or a substituted or unsubstituted aryl group having 6 to 15 ring carbon atoms.

X may be C, Si, or Ge.

$Y_1$ and $Y_2$ may each independently be $CR_6R_7$ or $SiR_8R_9$.

The polycyclic compound represented by Formula 1 may be a compound of the following Compound Group 1:

[Compound Group 1]

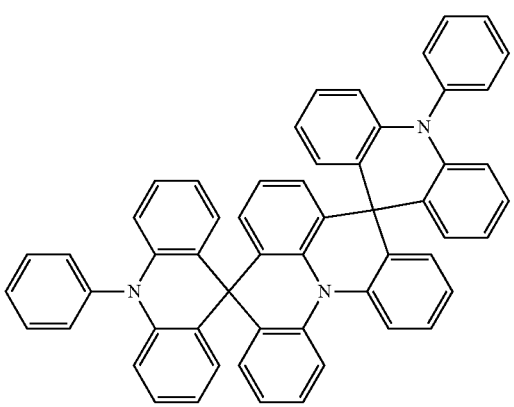

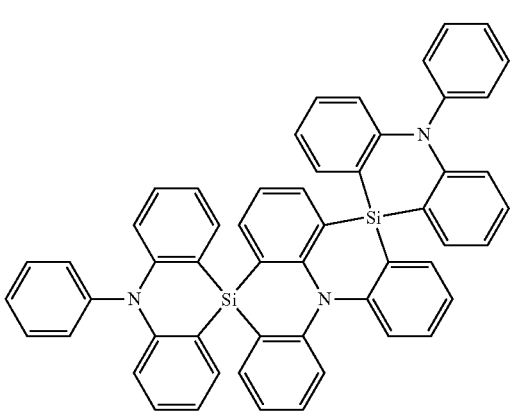

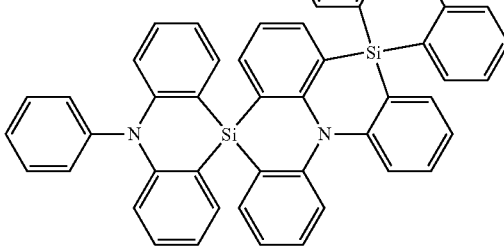

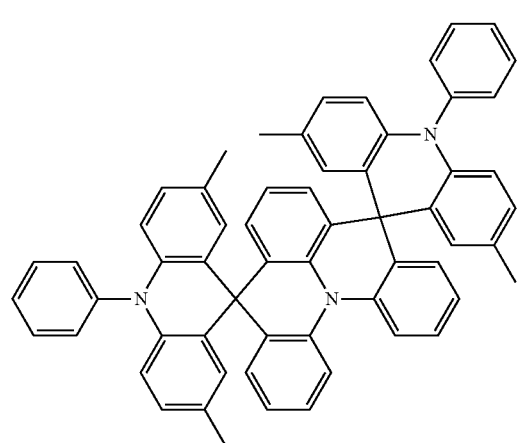
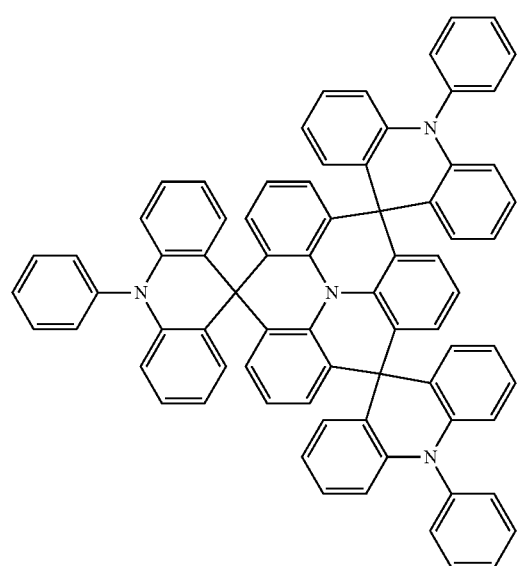
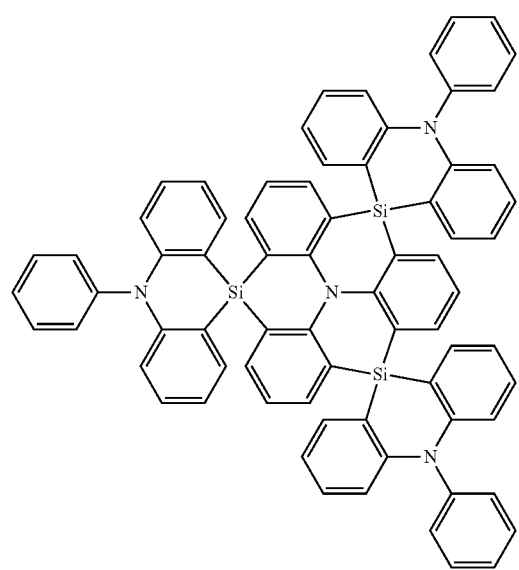
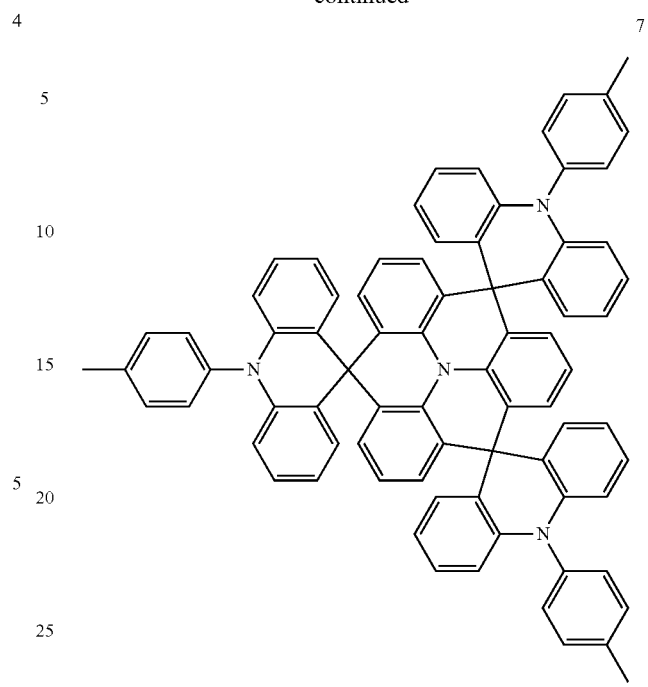
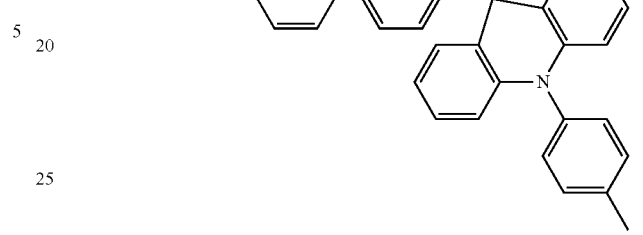
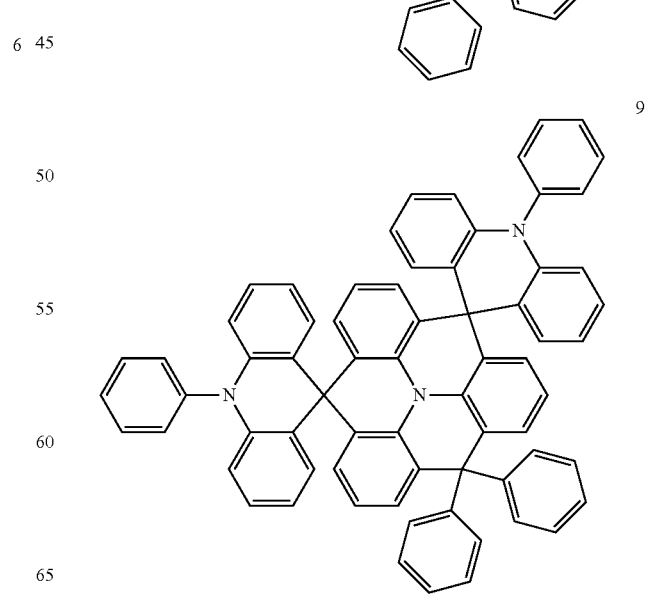

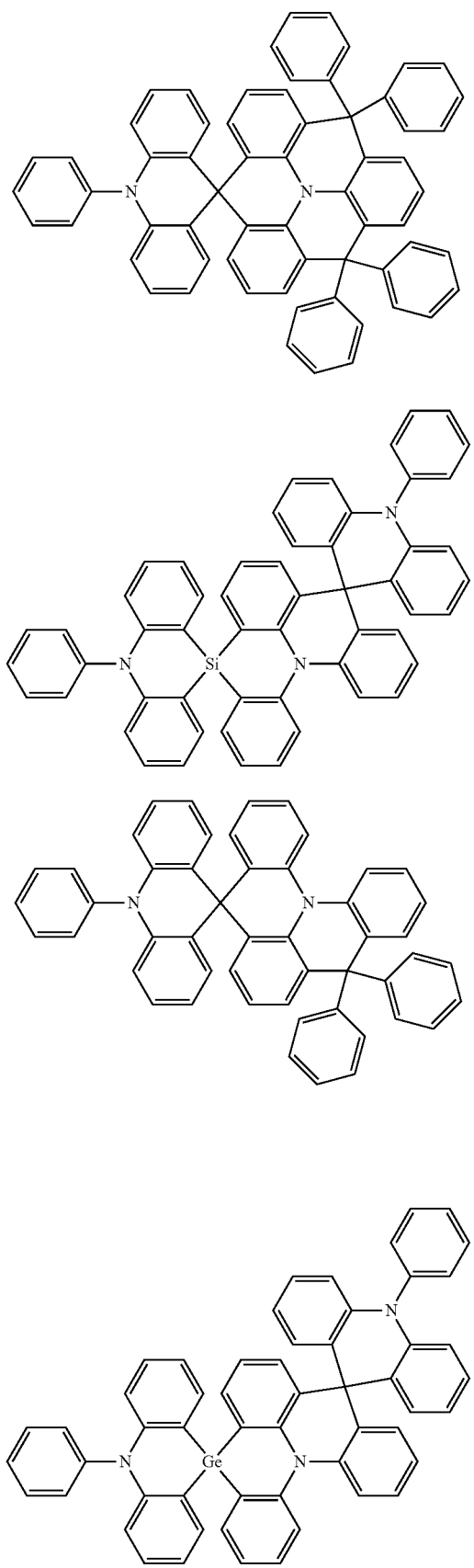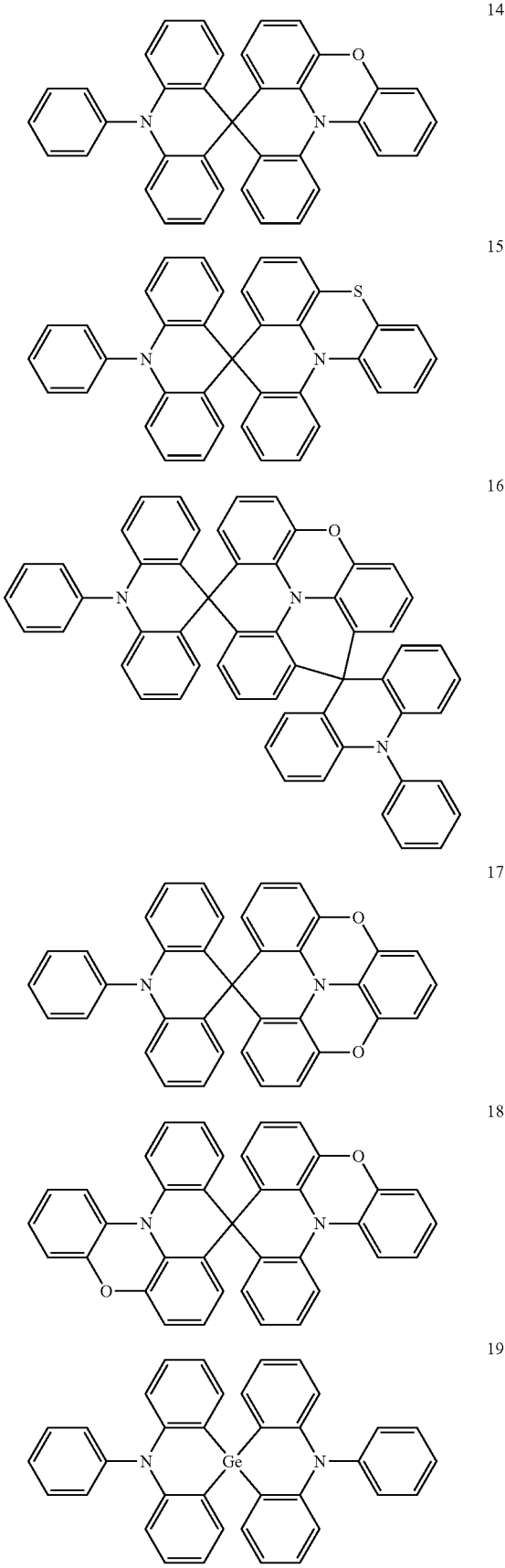

-continued

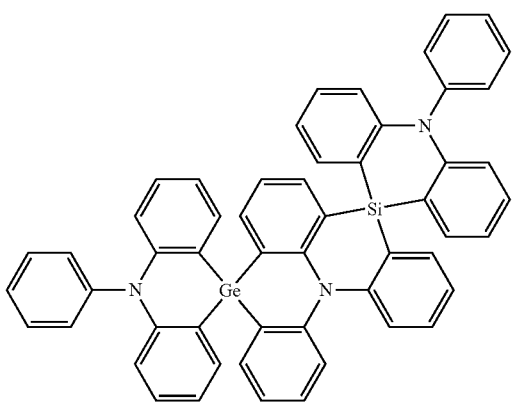

The polycyclic compound represented by Formula 1 may be a thermally activated delayed fluorescence (TADF) luminescence material or a phosphorescence luminescence material.

BRIEF DESCRIPTION OF THE FIGURES

Features will be apparent to those of skill in the art by describing in detail exemplary embodiments with reference to the attached drawings in which.

DETAILED DESCRIPTION

Figure 1:
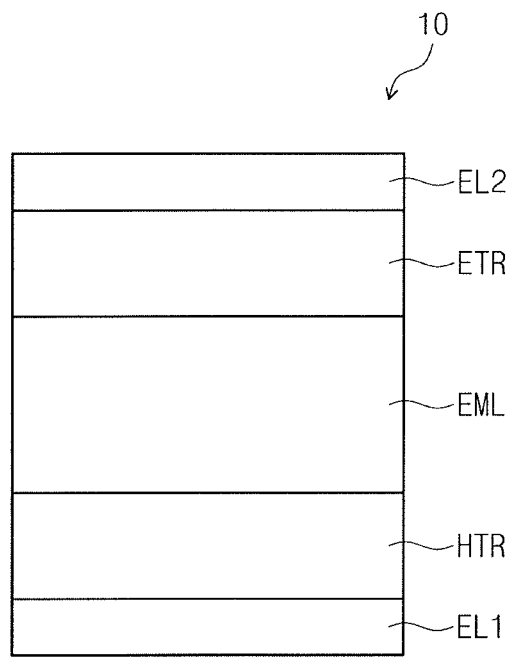
FIG. 1 illustrates a schematic cross-sectional view of an organic electroluminescence device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration.

Like reference numerals refer to like elements for explaining each drawing. In the drawings, the sizes of elements may be enlarged for clarity of the inventive concept. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "includes," "including," "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be directly on the other part, or intervening layers may also be present. On the contrary, when a layer, a film, a region, a plate, etc. is referred to as being "under" another part, it can be directly under the other part, or intervening layers may also be present.

In the present disclosure,

means a part to be connected, e.g., a bonding site.

In the present disclosure, "substituted or unsubstituted" may mean unsubstituted or substituted with at least one substituent selected from the group consisting of deuterium, halogen, cyano, nitro, amino, silyl, boron, arylamine, phosphine oxide, phosphine sulfide, alkyl, alkenyl, aryl and heterocycle group. In addition, each of the substituent illustrated above may be substituted or unsubstituted. For example, biphenyl may be interpreted as aryl, or phenyl substituted with phenyl.

In the present disclosure, the description of forming a ring by combining adjacent groups with each other may mean forming a substituted or unsubstituted hydrocarbon ring or a substituted or unsubstituted heterocycle by combining adjacent groups with each other. A hydrocarbon ring includes an aliphatic hydrocarbon ring and an aromatic hydrocarbon ring. The heterocycle includes an aliphatic heterocycle and an aromatic heterocycle. The hydrocarbon ring and heterocycle may be a monocycle or polycycle. In addition, the ring formed by combining adjacent groups with each other may be connected with another ring to form a spiro structure.

In the present disclosure, "an adjacent group" may mean a substituent at an atom which is directly connected with another atom at which a corresponding substituent is substituted, another substituent at an atom at which a corresponding substituent is substituted, or a substituent stereoscopically disposed at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, examples of a halogen atom are a fluorine atom, a chlorine atom, a bromine atom, or an iodine atom.

In the present disclosure, the alkyl group may have a linear, branched or cyclic form. The carbon number of the alkyl group may be 1 to 30, 1 to 20, 1 to 15, 1 to 10 or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl. 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group means any functional group or substituent derived from an aromatic hydrocarbon ring. The aryl group may be monocyclic aryl or polycyclic aryl. The carbon number of the aryl group for forming a ring may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc., without limitation.

In the present disclosure, the fluorenyl group may be substituted, and two substituents may be combined with each other to form a spiro structure.

In the present disclosure, the heteroaryl group may be heteroaryl including at least one of O, N, P, S, Si or Ge as a heteroatom. The carbon number of the heteroaryl group for forming a ring may be 2 to 30, or 2 to 20. Examples of the heteroaryl group may include thiophenyl, furanyl, pyrrolyl, imidazolyl, thiazolyl, oxazolyl, oxadiazolyl, triazolyl, pyridyl, bipyridyl, pyrimidyl, triazinyl, triazolyl, acridyl, pyridazinyl, pyrazinyl, quinolinyl, quinazolinyl, quinoxalinyl, phenoxazyl, phthalazinyl, pyrido pyrimidinyl, pyrido pyrazinyl, pyrazino pyrazinyl, isoquinolinyl, indolyl, carbazolyl, N-arylcarbazolyl, N-heteroaryl carbazolyl, N-alkyl carbazolyl, benzoxazolyl, benzoimidazolyl, benzothiazolyl, benzocarbazolyl, benzothiophenyl, dibenzothiophenyl, thienothiophenyl, benzofuranyl, phenanthrolinyl, thiazolyl, isoxazolyl, oxadiazolyl, thiadiazolyl, benzothiazolyl, phenothiazinyl, dibenzofuranyl, etc., without limitation.

In the present disclosure, the silyl group may include alkyl silyl and aryl silyl. Examples of the silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc., without limitation.

In the present disclosure, the boron group may include alkyl boron and aryl boron. Examples of the boron group may include trimethyl boron, triethyl boron, t-butyl dimethyl boron, triphenyl boron, diphenyl boron, phenyl boron, etc., without limitation.

In the present disclosure, the alkenyl group may be linear or branched. The carbon number is not specifically limited, and may be 2 to 30, 2 to 20, or 2 to 10. Examples of the alkenyl group may include vinyl, 1-butenyl, 1-pentenyl, 1,3-butadienyl aryl, styrenyl, styrylvinyl, etc., without limitation.

In the present disclosure, the carbon number of the amine group is not specifically limited, and may be 1 to 30. The amine group may include alkyl amine and aryl amine. Examples of the amine group may include methylamine, dimethylamine, phenylamine, diphenylamine, naphthylamine, 9-methyl-anthracenylamine, triphenylamine, etc., without limitation.

Hereinafter, the polycyclic compound according to an embodiment will be explained.

In an implementation, the polycyclic compound according to an embodiment may be represented by the following Formula 1.

[Formula 1]

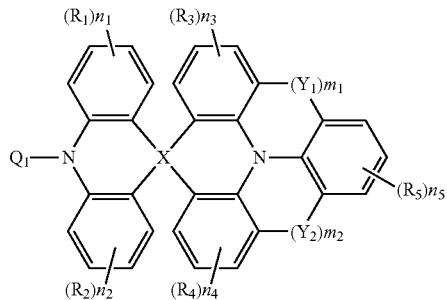

In Formula 1, X may be, e.g., C, Si, Ge, or Sn. In an implementation, X may be, e.g., C or Si.

$Y_1$ and $Y_2$ may each independently be, e.g., O, S, $CR_6R_7$, $SiR_8R_9$, $GeR_{10}R_{11}$, or $SnR_{12}R_{13}$. In an implementation, $Y_1$ and $Y_2$ may each independently be, e.g., $CR_6R_7$, or $SiR_8R_9$.

$R_1$ to $R_{13}$ may each independently be or include, e.g., a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group. In an implementation, $R_1$ to $R_{13}$ may form a ring by combining adjacent groups with each other. For example, $R_6$ may form a ring by combining with adjacent $R_7$, and $R_8$ may form a ring by combining with adjacent $R_9$. In an implementation, $R_1$ to $R_{13}$ may each independently be or include, e.g., a hydrogen atom, a substituted or unsubstituted alkyl group having 1 to 10 carbon atoms, or a substituted or unsubstituted aryl group having 6 to 15 ring carbon atoms. $R_1$ to $R_{13}$ may each independently be or include, e.g., a hydrogen atom or a substituted or unsubstituted phenyl group.

$n_1$ and $n_2$ may each independently be, e.g., an integer of 0 to 4. $n_3$ to $n_5$ may each independently be, e.g., an integer of 0 to 3. In an implementation, $n_1$ to $n_5$ may each independently be, e.g., 0 or 1. In an implementation, each of $n_1$ to $n_5$ may be 0. When each of $n_1$ to $n_5$ is 0, this may be substantially the same as each of $R_1$ to $R_5$ is a hydrogen atom.

In case $n_1$ is 2, 3, or 4, the 2, 3, or 4 $R_1$ may be the same or different from each other. In case $n_2$ is 2, 3, or 4, the 2, 3, or 4 $R_2$ may be the same or different from each other. In case $n_3$ is 2 or 3, the 2 or 3 $R_3$ may be the same or different from each other. In case $n_4$ is 2 or 3, the 2 or 3 $R_4$ may be the same or different from each other. In case $n_5$ is 2 or 3, the 2 or 3 $R_5$ may be the same or different from each other.

$Q_1$ may be or may include, e.g., a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $Q_1$ may be or may include, e.g., a substituted or unsubstituted alkyl group having 1 to 10 carbon atoms, or a substituted or unsubstituted aryl group having 6 to 15 ring carbon atoms. In an implementation, $Q_1$ may be or may include, e.g., a substituted or unsubstituted methyl or a substituted or unsubstituted phenyl. In an implementation, $Q_1$ may form a ring by combining adjacent groups with each other.

$m_1$ and $m_2$ may each independently be, e.g., 0 or 1. In an implementation, when X is C or Si, at least one of $m_1$ or $m_2$ may be 1. In an implementation, when X is C or Si, provided that $m_1$ is 0, $m_2$ is an integer of 1. In an implementation, when X is C or Si, provided that $m_1$ is 1, $m_2$ is 0 or 1. A case where X is C or Si and both of $m_1$ and $m_2$ are 0, is excluded. In an implementation, when X is Ge or Sn, both of $m_1$ and $m_2$ may be 0.

In an implementation, $Y_1$ and $Y_2$ may each independently be, e.g., a group represented by the following Formula 2.

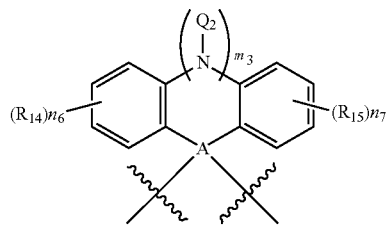

[Formula 2]

In Formula 2, A may be, e.g., C, Si, Ge, or Sn. In an implementation, A may be, e.g., C or Si.

$R_{14}$ and $R_{15}$ may each independently be or include, e.g., a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group. In an implementation, $R_{14}$ and $R_{15}$ may form a ring by combining adjacent groups with each other.

$n_6$ and $n_7$ may each independently be, e.g., an integer of 0 to 4. In an implementation, $n_6$ and $n_7$ may each independently be, e.g., 0 or 1.

$Q_2$ may be or may include, e.g., a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $Q_2$ may be or may include, e.g., a substituted or unsubstituted alkyl group having 1 to 10 carbon atoms or a substituted or unsubstituted aryl group having 6 to 15 ring carbon atoms. In an implementation, $Q_2$ may be or may include, e.g., a substituted or unsubstituted methyl or a substituted or unsubstituted phenyl.

$m_3$ may be, e.g., 0 or 1. In case $m_3$ is 0, $Y_1$ and $Y_2$ may have a structure where two substituted or unsubstituted phenyl groups are substituted at C or Si. In case $m_3$ is 1, $Y_1$ and $Y_2$ may be a substituted or unsubstituted acridine or a substituted or unsubstituted phenazasiline.

In an implementation, $Y_1$ and $Y_2$ represented by Formula 2 may each independently be, e.g., a group represented by the following Formula 2-1 or 2-2.

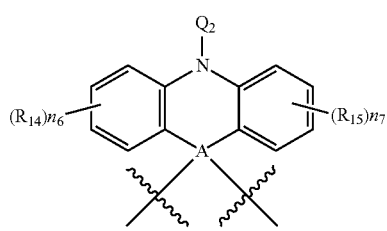

[Formula 2-1]

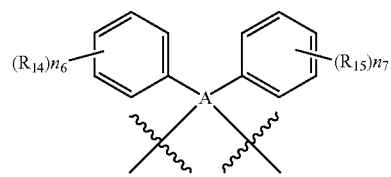

[Formula 2-2]

In Formulae 2-1 and 2-2, A, $R_{14}$, $R_{15}$ and $Q_2$ are the same as defined in Formula 2.

In $Y_1$ and $Y_2$ represented by Formula 2, when $m_3$ is 1, $Y_1$ and $Y_2$ may each independently be, e.g., a group represented by Formula 2-1. When $m_3$ is 0, $Y_1$ and $Y_2$ may each independently be, e.g., a group represented by Formula 2-2.

$Y_1$ and $Y_2$ may be the same or different from each other. In an implementation, both of $Y_1$ and $Y_2$ may be represented by Formula 2-1. In an implementation, $Y_1$ may be represented by Formula 2-1, and $Y_2$ may be represented by Formula 2-2. In an implementation, both of $Y_1$ and $Y_2$ may be represented by Formula 2-2.

In an implementation, the polycyclic compound represented by Formula 1 may be represented by any one of the following Formulae 3-1 to 3-6.

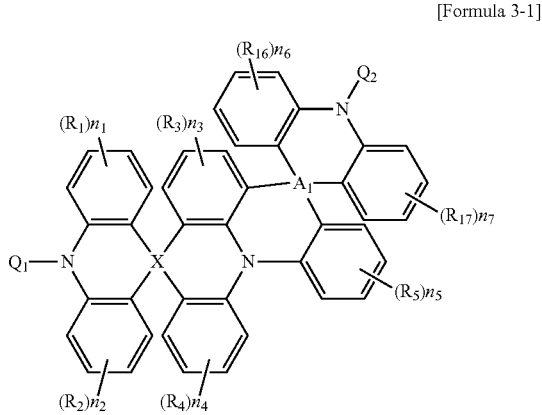

[Formula 3-1]

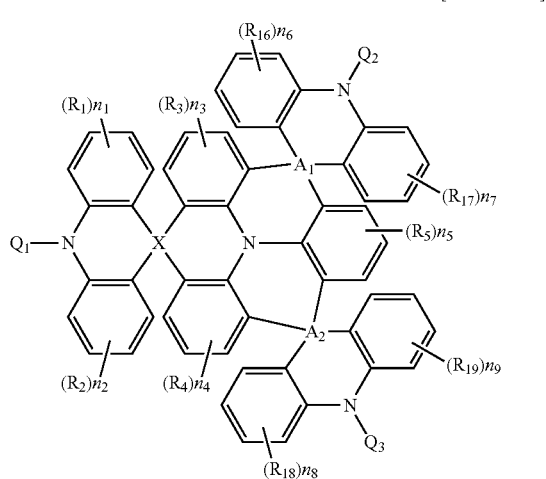

[Formula 3-2]

[Formula 3-3]

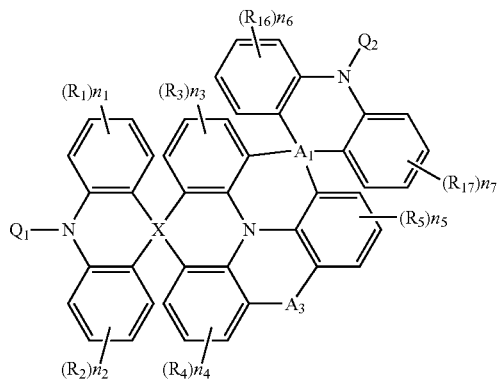

[Formula 3-4]

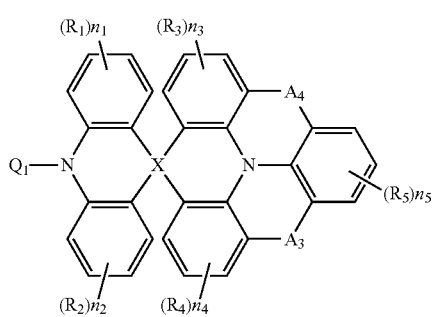

[Formula 3-5]

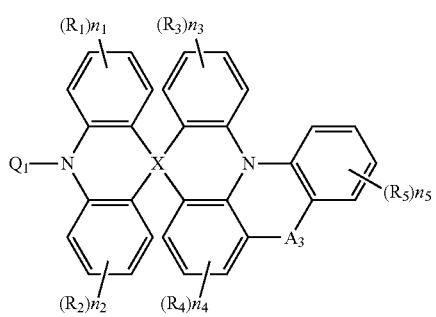

[Formula 3-6]

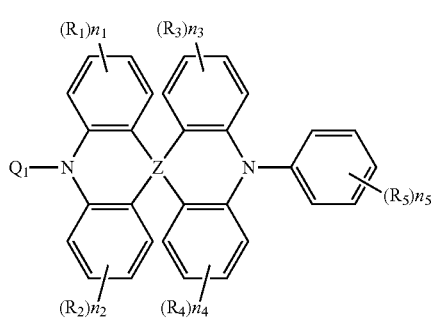

In Formulae 3-1 to 3-6, X, $Q_1$, $R_1$ to $R_5$, and $n_1$ to $n_5$ are the same as defined above.

$A_1$ and $A_2$ may each independently be, e.g., C, Si, Ge, or Sn. In an implementation, $A_1$ and $A_2$ may each independently be, e.g., C or Si. $A_1$ and $A_2$ may be the same or different from each other. In an implementation, both of $A_1$ and $A_2$ may be C. In an implementation, $A_1$ may be C and $A_2$ may be Si.

$A_1$ and $A_2$ may be the same as or different from X. In an implementation, each of $A_1$, $A_2$ and X may be equally C or Si. In an implementation, X may be Si, and each of $A_1$ and $A_2$ may be C.

$A_3$ and $A_4$ may each independently be, e.g., O, S, $CR_{20}R_{21}$, $SiR_{22}R_{23}$, $GeR_{24}R_{25}$, or $SnR_{26}R_{27}$. In an implementation, $A_3$ and $A_4$ may each independently be, e.g., O, S, $CR_{20}R_{21}$, or $SiR_{22}R_{23}$. $A_3$ and $A_4$ may be the same or different from each other.

$R_{16}$ to $R_{27}$ may each independently be or include, e.g., a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group. In an implementation, $R_{16}$ to $R_{27}$ may form a ring by combining adjacent groups with each other. In an implementation, the adjacent $R_{18}$ and $R_{19}$ may combine with each other to form a ring.

In an implementation, $R_{16}$ to $R_{27}$ may each independently be or include, e.g., a hydrogen atom, a substituted or unsubstituted alkyl group having 1 to 10 carbon atoms, or a substituted or unsubstituted aryl group having 6 to 15 ring carbon atoms ring. In an implementation, at least one of $R_{16}$ to $R_{27}$ may be or include, e.g., a substituted or unsubstituted methyl, or a substituted or unsubstituted phenyl. In an implementation, $R_{16}$ and $R_{17}$ may be, e.g., an unsubstituted methyl. $R_{16}$ to $R_{27}$ may be the same or different from each other.

Z may be, e.g., Ge or Sn. In an implementation, Z may be, e.g., Ge.

$n_6$ to $n_9$ may each independently be, e.g., an integer of 0 to 4. In case $n_6$ is 2, 3, or 4, the 2, 3, or 4 $R_{16}$ may be the same or different from each other. In case $n_7$ is 2, 3, or 4, the 2, 3, or 4 $R_{17}$ may be the same or different from each other. In case $n_8$ is 2, 3, or 4, the 2, 3, or 4 $R_{18}$ may be the same or different from each other. In case $n_9$ is 2, 3, or 4, the 2, 3, or 4 $R_{19}$ may be the same or different from each other.

$Q_2$ and $Q_3$ may each independently be or include, e.g., a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $Q_2$ and $Q_3$ may each independently be or include, e.g., a substituted or unsubstituted alkyl group having 1 to 10 carbon atoms or a substituted or unsubstituted aryl group having 6 to 15 ring carbon atoms. In an implementation, $Q_2$ and $Q_3$ may each independently be or include, e.g., a substituted or unsubstituted methyl or a substituted or unsubstituted phenyl.

$Q_1$ to $Q_3$ may be the same or different from each other. In an implementation, each of $Q_1$ to $Q_3$ may be, e.g., a substituted or unsubstituted aryl group having 6 to 15 carbon atoms for forming a ring. In an implementation, each of $Q_1$ to $Q_3$ may be, e.g., an unsubstituted phenyl. In an implementation, each of $Q_1$ to $Q_3$ may be, e.g., a phenyl group substituted with one methyl group.

In Formula 1, when both of $m_1$ and $m_2$ are 1, the polycyclic compound represented by Formula 1 may be represented by Formula 3-2, 3-3, or 3-4. In Formula 1, when any one of $m_1$ and $m_2$ is 1 and the other is 0, the polycyclic compound represented by Formula 1 may be represented by Formula 3-1 or 3-5.

In Formula 1, when X is Ge or Sn, both of $m_1$ and $m_2$ may be 0. In Formula 1, when X is Ge or Sn, the polycyclic compound represented by Formula 1 may be represented by Formula 3-6.
In an implementation, the polycyclic compound represented by Formula 1 may be, e.g., a compound the following Compound Group 1.
[Compound Group 1]
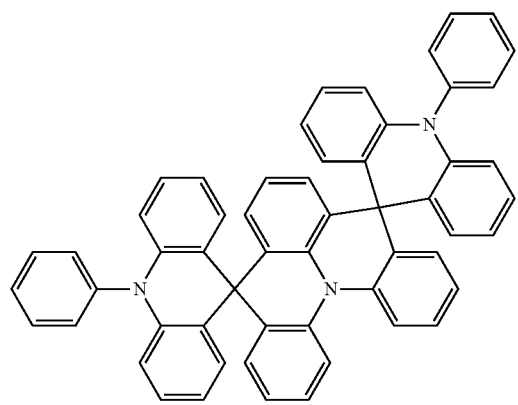
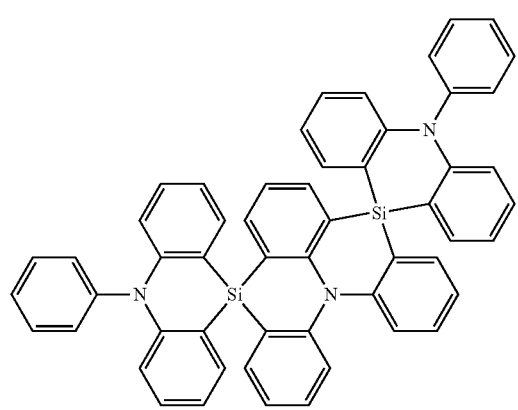
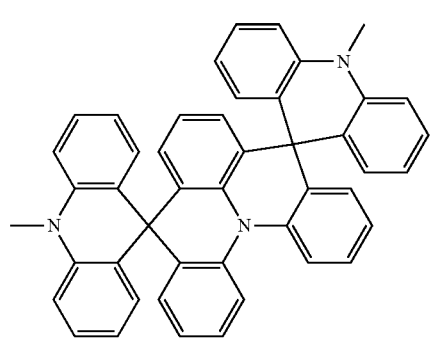
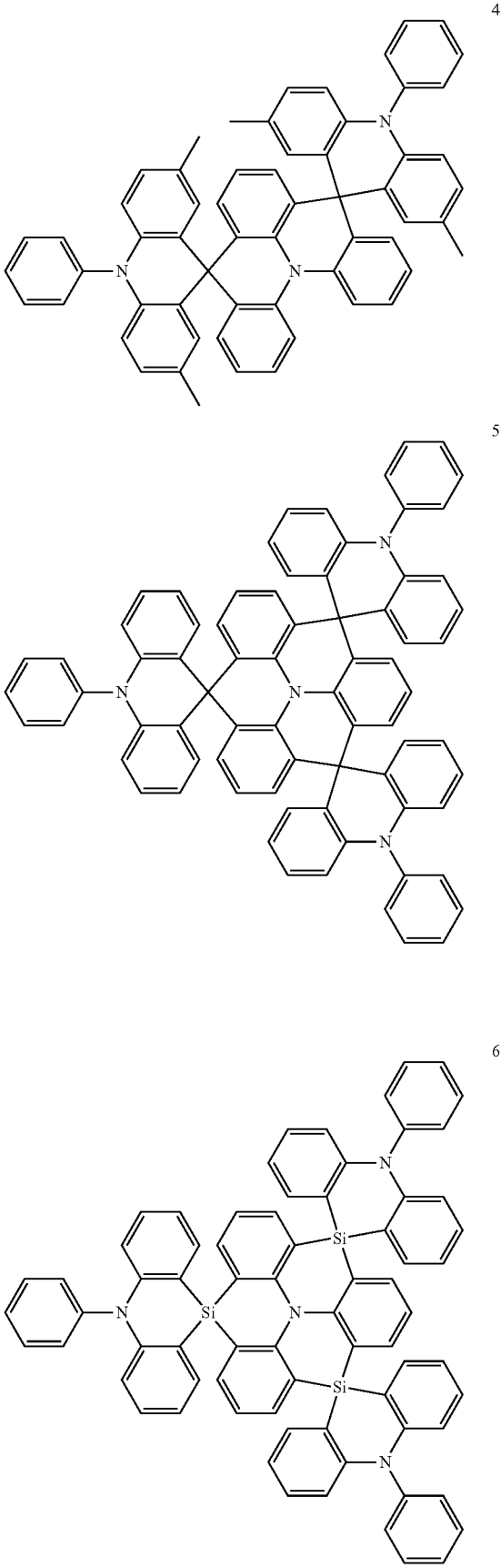

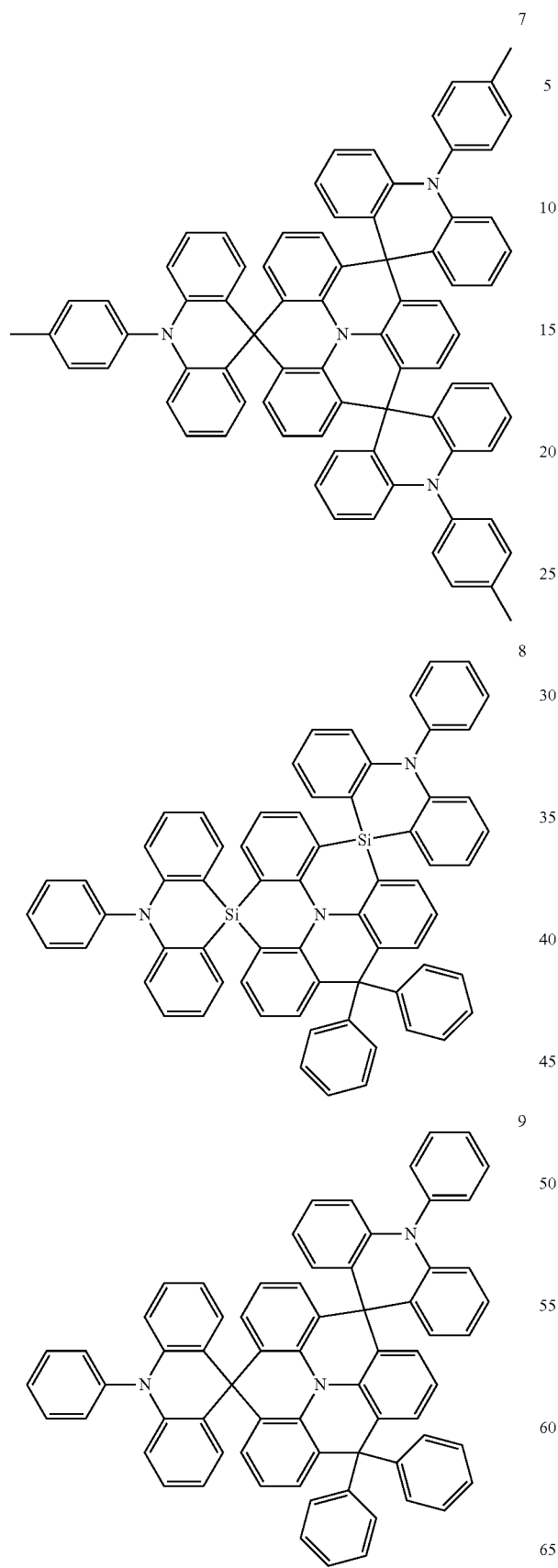
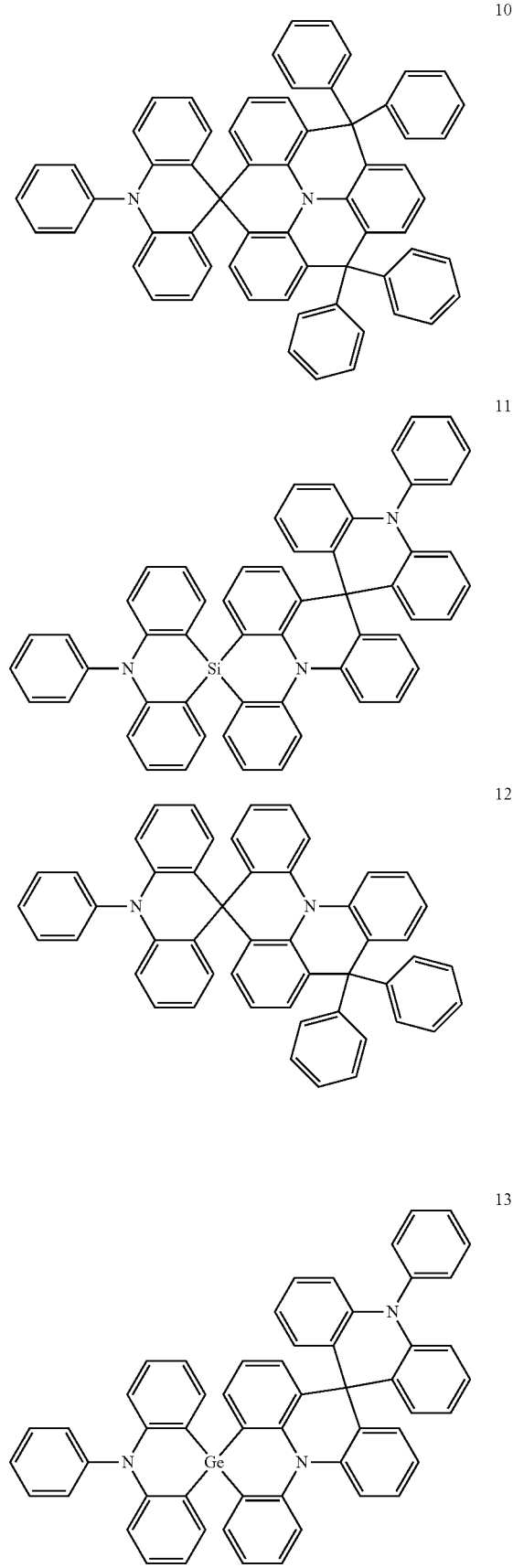

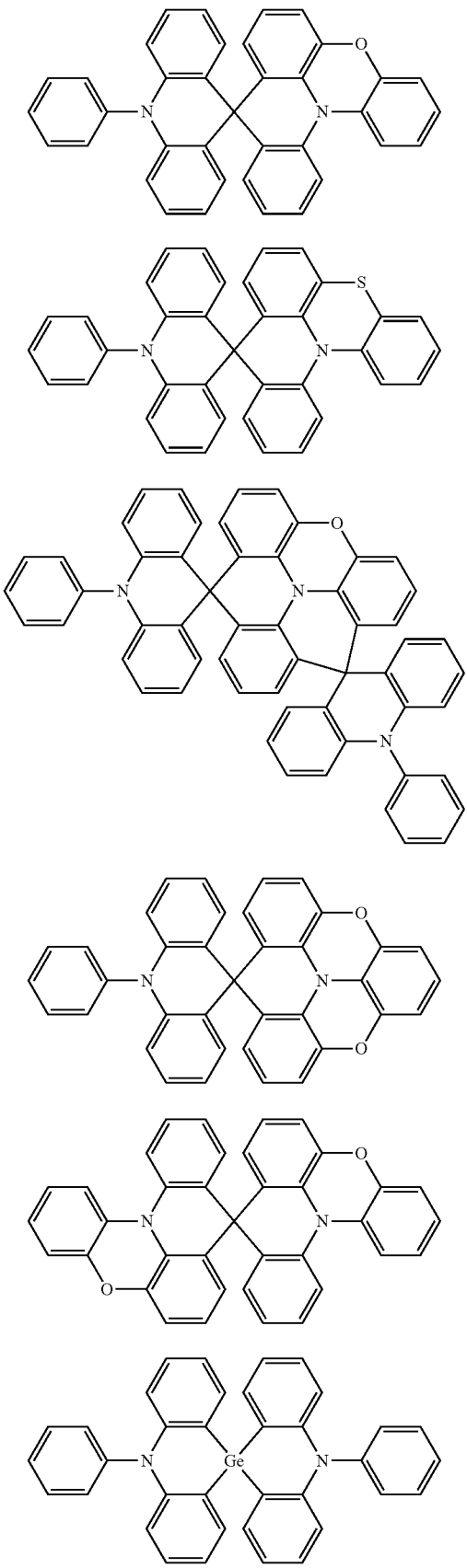
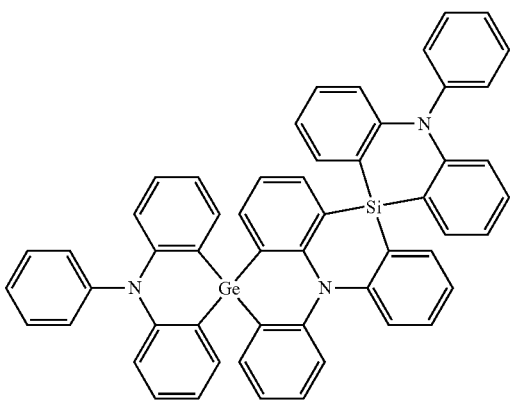

When the polycyclic compound according to an embodiment is applied to an organic electroluminescence device, high emission efficiency and a low driving voltage may be secured.

For example, the polycyclic compound represented by Formula 1 may have a high level of the lowest triplet excitation energy (T1) and a high level of the highest occupied molecular orbital (HOMO) energy. For example, the polycyclic compound according to an embodiment may be disposed in a hole transport region of an organic electroluminescence device to have a high hole transport property for an efficient hole transport and to inhibit the diffusion of triplet excitons generated in an emission layer into a hole transport region, thereby securing high emission efficiency of an organic electroluminescence device.

Hereinafter, an organic electroluminescence device according to an embodiment will be explained. The explanation will be mainly given with features different from the polycyclic compound according to an embodiment, and unexplained parts will follow the above-description on the polycyclic compound according to an embodiment.

An organic electroluminescence device according to an embodiment may include the above-mentioned polycyclic compound according to an embodiment.

Figure 2:
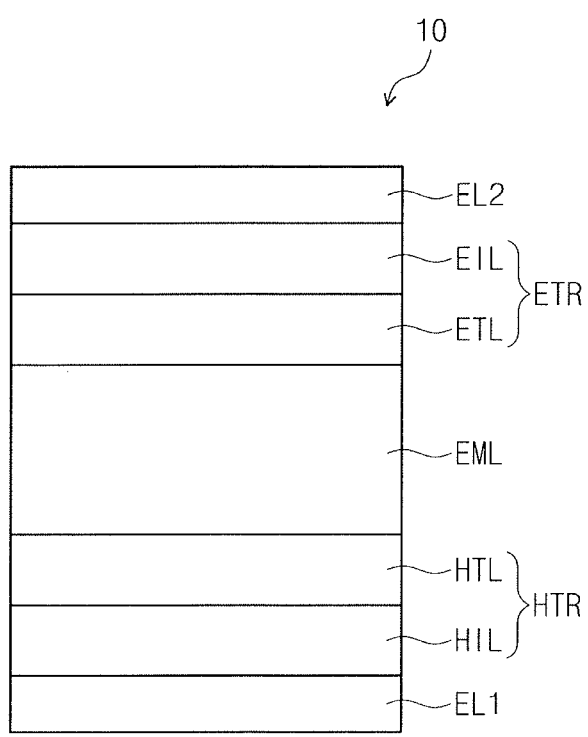
FIG. 2 illustrates a schematic cross-sectional view of an organic electroluminescence device according to an embodiment.
Figure 3:
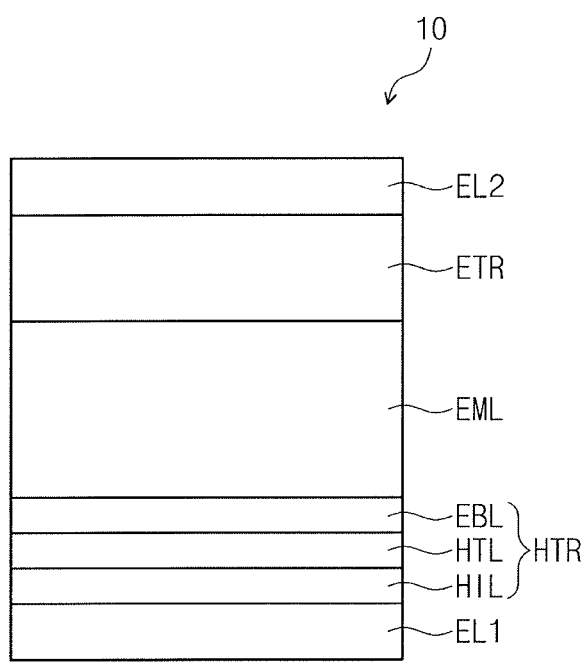
FIG. 3 illustrates a schematic cross-sectional view of an organic electroluminescence device according to an embodiment.

FIG. 1 illustrates a schematic cross-sectional view of an organic electroluminescence device according to an embodiment. FIG. 2 illustrates a schematic cross-sectional view of an organic electroluminescence device according to an embodiment. FIG. 3 illustrates a schematic cross-sectional view of an organic electroluminescence device according to an embodiment.

Referring to FIGS. 1 to 3, an organic electroluminescence device 10 according to an embodiment may include a first electrode EL1, a hole transport region HTR, an emission layer EML, an electron transport region ETR, and a second electrode EL2.

The first electrode EL1 has conductivity. The first electrode EL1 may be a pixel electrode or an anode. The first electrode EL1 may be a transmissive electrode, a transflective electrode, or a reflective electrode. In case the first electrode EL1 is the transmissive electrode, the first electrode EL1 may include a transparent metal oxide such as indium tin oxide (ITO), indium zinc oxide (IZO), zinc oxide (ZnO), or indium tin zinc oxide (ITZO). In case the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or transflective layer formed using the above materials, and a transparent conductive layer formed using ITO, IZO, ZnO, or ITZO.

Hereinafter, a case where the polycyclic compound according to an embodiment is included in a hole transport region HTR, will be explained. In an implementation, the polycyclic compound according to an embodiment may be included in at least one organic layer provided between the first electrode EL1 and the second electrode EL2.

The organic electroluminescence device according to an embodiment may include the polycyclic compound represented by the following Formula 1 in the hole transport region HTR. The hole transport region HTR may include one or more of the polycyclic compound represented by Formula 1.

[Formula 1]

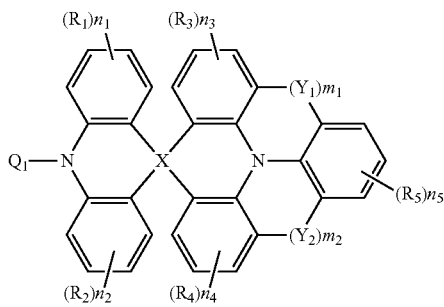

In Formula 1, particular explanation on X, $R_1$ to $R_5$, $Q_1$, $Y_1$, $Y_2$, $n_1$ to $n_5$, $m_1$ and $m_2$ is the same as described above, and will be omitted.

Particular explanation on the polycyclic compound represented by Formula 1 may directly refer to the above description, and will be omitted.

The hole transport region HTR may be disposed on the first electrode EL1. The hole transport region HTR may include, e.g., at least one of a hole injection layer HIL, a hole transport layer HTL, a hole buffer layer, or an electron blocking layer. The thickness of the hole transport region HTR may be, e.g., from about 1,000 Å to about 1,500 Å.

The hole transport region HTR may have, e.g., a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In an implementation, the hole transport region HTR may have, e.g., a single layer structure formed using a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, laminated in order from the first electrode EL1.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

In an implementation, the hole transport region HTR may include the polycyclic compound according to an embodiment as a hole transport material. In an implementation, the layer including the polycyclic compound according to an embodiment may be a layer adjacent to the emission layer EML. In an implementation, as shown in FIG. 2, when the hole transport layer HTL in the hole transport region HTR is adjacent to the emission layer EML, the hole transport layer HTL, may include the polycyclic compound according to an embodiment. In an implementation, as shown in FIG. 3, when an electron blocking layer EBL is further included on the hole transport layer HTL in the hole transport region HTR, the electron blocking layer EBL may include the polycyclic compound according to an embodiment. At least one of the hole transport layer HTL or the electron blocking layer EBL may include one or more of the polycyclic compound represented by Formula 1. The hole transport layer HTL and the electron blocking layer EBL may further include a suitable material in addition to the polycyclic compound represented by Formula 1.

In case the hole transport layer HTL or the electron blocking layer EBL includes the polycyclic compound according to an embodiment, the hole injection layer HIL may include, e.g., a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalen-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

In case the hole transport layer HTL does not includes the polycyclic compound according to an embodiment, and, e.g., the electron blocking layer EBL includes the polycyclic compound according to an embodiment, the hole transport layer HTL may include, e.g., carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4''-tris(N-carbazolyl)triphenylamine (TCTA), N,N'-di(1-naphthalen-1-yl)-N,N'-diphenyl-benzidine (NPB), 4,4'-cyclohexylidene bis[N,N-bis(4-methylphenyl)benzenamine](TAPC), 4,4'-bis[N,N'-(3-tolyl)amino]-3,3'-dimethylbiphenyl (HMTPD), etc.

The thickness of the hole transport region HTR may be from about 100 Å to about 10,000 Å, e.g., from about 100 Å to about 1,000 Å. In case the hole transport region HTR includes both of the hole injection layer HIL and the hole transport layer HTL, the thickness of the hole injection layer HIL may be from about 100 Å to about 10,000 Å, e.g., from about 100 Å to about 1,000 Å, and the thickness of the hole transport layer I-HTL may be from about 30 Å to about 1,000 Å. In case the thicknesses of the hole transport region HTR, the hole injection layer HIL and the hole transport layer HTL satisfy the above-described ranges, satisfactory hole transport properties may be obtained without the substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, e.g., a p-dopant. The p-dopant may be one of quinone derivatives, metal oxides, or cyano group-containing compounds. Examples of the p-dopant may include quinone derivatives such as tetracyanoquinodimethane (TCNQ) and 2,3,5,6-tetrafluoro-tetracyanoquinodimethane (F4-TCNQ), metal oxides such as tungsten oxide and molybdenum oxide.

The hole transport region HTR may further include at least one of the hole buffer layer or the electron blocking layer EBL in addition to the hole injection layer HIL and the hole transport layer HTL, as described above. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer EBL is a layer preventing electron injection from the electron transport region ETR into the hole transport region HTR.

The emission layer EML may be disposed on the hole transport region HTR. The thickness of the emission layer EML may be, e.g., from about 100 Å to about 300 Å. The emission layer EML may have, e.g., a single layer formed using a single material, a single layer formed using a plurality of different materials, or a multilayer structure having a plurality of layers formed using a plurality of different materials.

The emission layer EML may emit one of red light, green light, blue light, white light, yellow light, or cyan light. The emission layer EML may include a fluorescent material or a phosphorescent material. The emission layer EML may include a host and a dopant. The thickness of the emission layer EML may be, for example, from about 10 nm to about 60 nm.

The host may include a suitable material, e.g., tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), etc.

The dopant may include, e.g., styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi)), perylene and the derivatives thereof (for example, 2,5,8,11-tetra-tert-butylperylene (TBP)), pyrene and the derivatives thereof (for example, 1,1-dipyrene, 1,4-dipyrenylbenzene, 1,4-bis(N,N-diphenylamino)pyrene), etc.

When the emission layer EML emits red light, the emission layer EML may further include a fluorescent material including, e.g., tris(dibenzoylmethanato)phenanthroline europium ($PBD:Eu(DBM)_3(Phen)$), or a fluorescent material including perylene. In case the emission layer EML emits red light, the dopant included in the emission layer EML may be selected from, e.g., a metal complex or an organometallic complex such as bis(1-phenylisoquinoline)acetylacetonate iridium (PIQIr(acac)), bis(1-phenylquinoline)acetylacetonate iridium (PQIr(acac), tris(1-phenylquinoline)iridium (PQIr), and octaethylporphyrin platinum (PtOEP), rubrene and the derivatives thereof, and 4-dicyanomethylene-2-(p-dimethylaminostyryl)-6-methyl-4H-pyran (DCM) and the derivatives thereof.

When the emission layer EML emits green light, the emission layer EML may further include a fluorescent material including, e.g., tris(8-hydroxyquinolino)aluminum ($Alq_3$). In case the emission layer EML emits green light, the dopant included in the emission layer EML may be selected from, e.g., a metal complex or organometallic complex such as fac-tris(2-phenylpyridine)iridium ($Ir(ppy)_3$), and coumarin and the derivatives thereof.

When the emission layer EML emits blue light, the emission layer EML may further include a fluorescent material including any one selected from, e.g., spiro-DPVBi, spiro-6P, distyryl-benzene (DSB), distyryl-arylene (DSA), a polyfluorene (PFO)-based polymer, and a poly(p-phenylene vinylene) (PPV)-based polymer. In case the emission layer EML emits blue light, the dopant included in the emission layer EML may be selected from, e.g., a metal complex or an organometallic complexes such as (4,6-$F_2$ppy)2Irpic, perylene and the derivatives thereof, 10-phenyl-10H,10'H-spiro[acridine-9,9'-anthracen]-10'-one (ACRSA), etc.

The electron transport region ETR may be disposed on the emission layer EML. The electron transport region ETR may include, e.g., at least one of a hole blocking layer, an electron transport layer ETL or an electron injection layer EIL.

The electron transport region ETR may have, e.g., a single layer formed using a single material, a single layer formed using a plurality of different materials, or a multilayer structure having a plurality of layers formed using a plurality of different materials.

For example, the electron transport region ETR may have a single layer structure of the electron injection layer EIL or the electron transport layer ETL, or a single layer structure formed using an electron injection material and an electron transport material. In an implementation, the electron transport region ETR may have, e.g., a single layer structure having a plurality of different materials, or a laminated structure of electron transport layer ETL/electron injection layer EIL, or hole blocking layer/electron transport layer ETL/electron injection layer EIL, laminated in order from the emission layer EML. The thickness of the electron transport region ETR may be, e.g., from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In an implementation, in case the electron transport region ETR includes the electron transport layer ETL, the electron transport region ETR may include, e.g., tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen). 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato)

aluminum (BAlq), berylliumbis(benzoquinolin-10-olate (Bebq$_2$), 9,10-di(naphthalene-2-yl)anthracene (ADN), or a mixture thereof. The thickness of the electron transport layer ETL may be from about 100 Å to about 1,000 Å, e.g., from about 150 Å to about 500 Å. If the thickness of the electron transport layer ETL satisfies the above-described range, satisfactory electron transport properties may be obtained without substantial increase of a driving voltage.

In an implementation, when the electron transport region ETR includes the electron injection layer EIL, it may include a metal such as Al, Ag, Li, Mg and Ca, or a mixture thereof. In an implementation, the electron injection layer EIL may use, e.g., LiF, lithium quinolate (Liq), Li$_2$O, BaO, NaCl, CsF, a metal in lanthanides such as Yb, or a metal halide such as RbCl and RbI. The electron injection layer EIL also may be formed using a mixture material of an electron transport material and an insulating organo metal salt. The organo metal salt may be a material having an energy band gap of about 4 eV or more. In an implementation, the organo metal salt may include, e.g., a metal acetate, a metal benzoate, a metal acetoacetate, a metal acetylacetonate, or a metal stearate. The thickness of the electron injection layer EIL may be from about 1 Å to about 100 Å, e.g., from about 3 Å to about 90 Å. In case the thickness of the electron injection layer EIL satisfies the above described range, satisfactory electron injection properties may be obtained without inducing the substantial increase of a driving voltage.

The electron transport region ETR may include a hole blocking layer as described above. In an implementation, the hole blocking layer may include, e.g., at least one of 2,9-dimethyl-4,7-diphenyl-1,10-phenanthroline (BCP), 4,7-diphenyl-1,10-phenanthroline (Bphen), or bis[2-(diphenylphosphino)phenyl]ether oxide (DPEPO).

The second electrode EL2 may be disposed on the electron transport region ETR. The second electrode EL2 may be a common electrode or a cathode. The second electrode EL2 may be a transmissive electrode, a transflective electrode, or a reflective electrode. In case the second electrode EL2 is the transmissive electrode, the second electrode EL2 may be formed using transparent metal oxides, e.g., ITO, IZO, ZnO, ITZO, etc.

In case the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

In an implementation, the second electrode EL2 may be connected with an auxiliary electrode. In case the second electrode EL2 is connected with the auxiliary electrode, the resistance of the second electrode EL2 may decrease.

In the organic electroluminescence device 10, according to the application of a voltage to each of the first electrode EL1 and the second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to generate excitons, and light may be emitted via the transition of the excitons from an excited state to a ground state.

In case the organic electroluminescence device 10 is a top emission type, the first electrode EL1 may be a reflective electrode, and the second electrode EL2 may be a transmissive electrode or a transflective electrode. In case the organic electroluminescence device 10 is a bottom emission type, the first electrode EL1 may be a transmissive electrode or a transflective electrode, and the second electrode EL2 may be a reflective electrode.

The organic electroluminescence device according to an embodiment may include the polycyclic compound represented by Formula 1, thereby securing high emission efficiency and a low driving voltage. For example, the polycyclic compound represented by Formula 1 may be included in the hole transport region adjacent to the emission layer in the organic electroluminescence device. In case the polycyclic compound represented by Formula 1 is used as a hole transport material in the hole transport region adjacent to the emission layer, high hole transport properties may be secured, and the diffusion of triplet excitons generated in the emission layer into the hole transport region may be inhibited, thereby attaining high emission efficiency and a low driving voltage of an organic electroluminescence device.

The polycyclic compounds according to an embodiment may be synthesized, e.g., as follows.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis Examples

1. Synthesis of Compound 1

(Synthesis of Compound A)

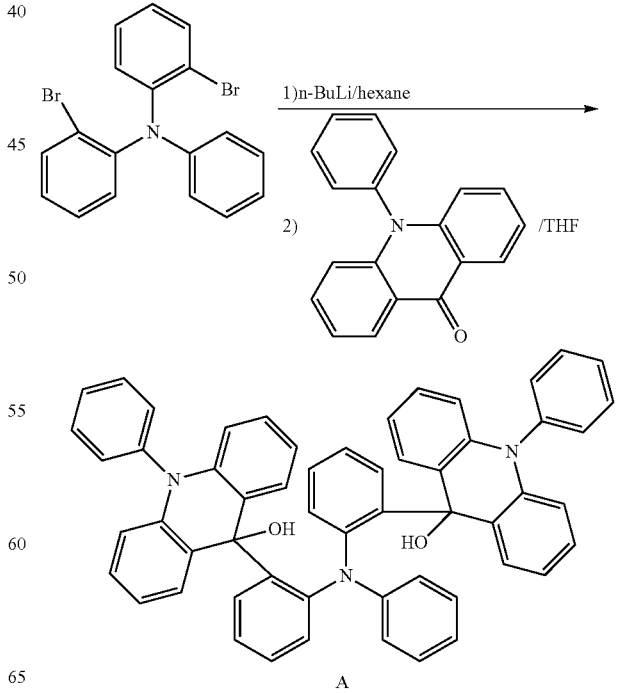

Under an argon (Ar) atmosphere, 15 mL of a hexane solution containing 1.6 mol/L n-BuLi was added to 100 mL of a THF solution containing 4.0 g of 2,2'-dibromo-triphenylamine cooled to about −78° C., and the mixture was stirred for about 1 hour. 50 mL of a THF solution containing 5.5 g of 10-phenylacridone was added thereto dropwise for about 1 hour under cooling condition, and the resultant was stirred at ambient temperature for about 6 hours. An aqueous ammonium oxide solution was added to the obtained reaction solution and the resultant was concentrated under vacuum. The residue was dissolved in methylene chloride and then purified by column chromatography to obtain 5.0 g (yield 64%) of Compound A as a white powder.

(Synthesis of Compound 1)

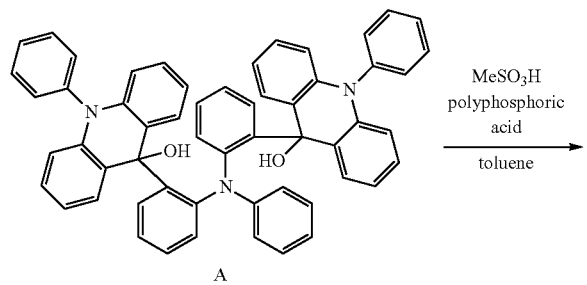

5.0 g of Compound A in toluene was heated in the presence of polyphosphoric acid at about 60° C. for about 6 hours. After cooling, the reactant was extracted with water-dichloromethane, and an organic layer was concentrated under reduced pressure. The residue was purified by column chromatography to obtain 2.4 g (yield 49%) of Compound 1 as a white powder. The molecular weight of Compound 1 measured by FAB-MS was 751. From the results, the compound thus synthesized was identified as Compound 1.

2. Synthesis of Compound 2

(Synthesis of Compound B)

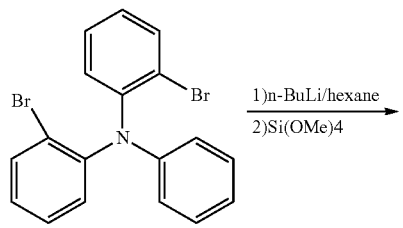

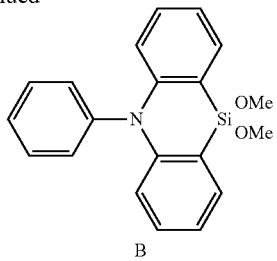

Under an argon atmosphere, 9.34 mL of a hexane solution containing 1.6 mol/L n-BuLi was added to 100 mL of a THF solution containing 3.0 g of 2,2'-dibromo-triphenylamine cooled to about −78° C., and the mixture was stirred for about 1 hour. 10 mL of a THF solution containing 1.5 g of tetramethoxysilane was added thereto at one time, and the resultant was heated to ambient temperature and then stirred for about 24 hours. Ethanol was added to the obtained reaction solution to stop the reaction and the resultant was extracted with dichloromethane and water. The extract was concentrated under reduced pressure to remove solvent and excess tetramethoxysilane and obtain 2.0 g (yield 80%) of Compound B as a colorless oil, which was used for the next reaction as it is.

(Synthesis of Compound 2)

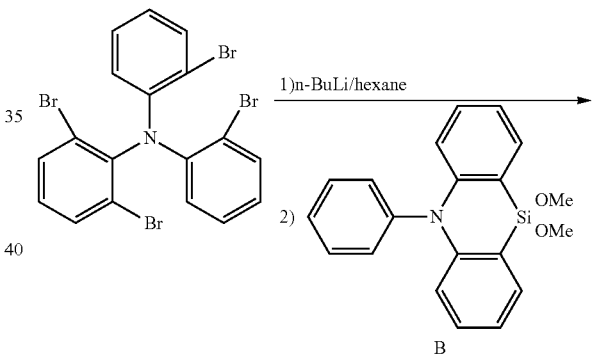

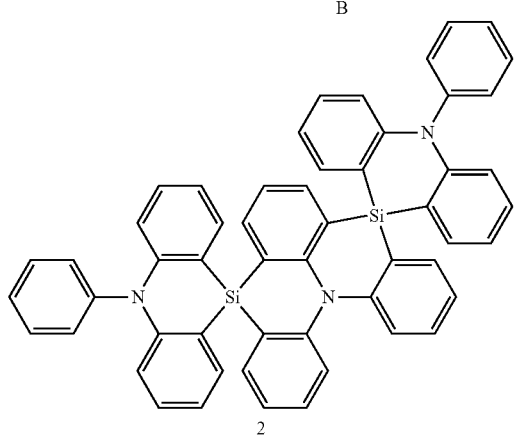

Under an argon atmosphere, 7.20 mL of a hexane solution containing 1.6 mol/L n-BuLi was added to 100 mL of a THF solution containing 1.5 g of 2,6,2'2''-tetrabromo-triphenylamine cooled to about −78° C. and the mixture was stirred for about 1 hour. 2.0 g of Compound B was added thereto dropwise, and the mixture was heated to ambient temperature and then stirred for about 24 hours. Ethanol was added to the obtained reaction solution to stop the reaction and the resultant was extracted with dichloromethane and water. An organic layer was concentrated under reduced pressure, and the residue was purified by column chromatography to obtain 0.63 g (yield 28%) of Compound 2 as a white crystal.

3. Synthesis of Compound 12

(Synthesis of Compound C)

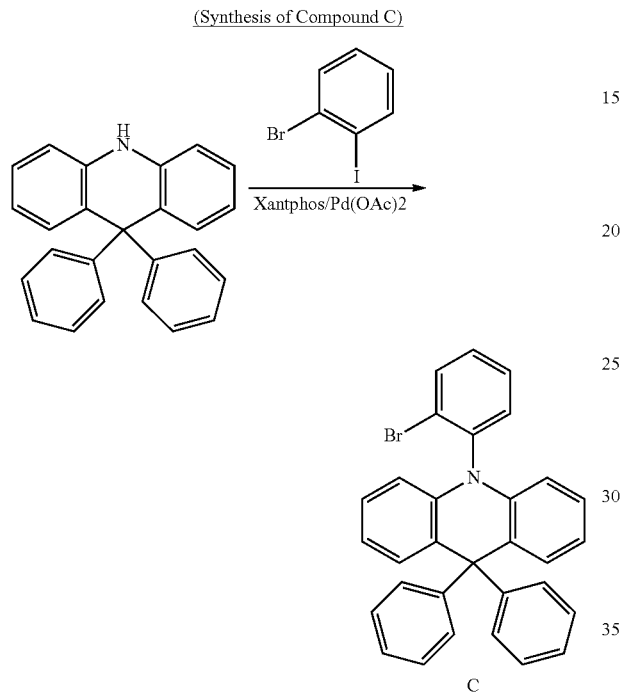

Under an argon (Ar) atmosphere, 4.0 g of 10,10'-diphenyldihydroacridine, 3.7 g of o-iodo-bromobenzene, 0.135 g of palladium acetate, 0.35 g of Xantphos, 2.31 g of NaOtBu and 100 mL of toluene was heated to reflux for about 8 hours. After cooling, the reaction solution was filtered, concentrated and the purified by column chromatography to obtain 4.1 g (yield 70%) of Compound C as a white powder.

(Synthesis of Compound D)

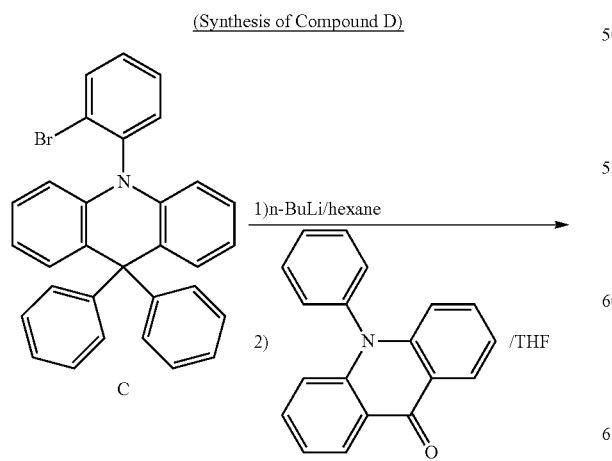

-continued

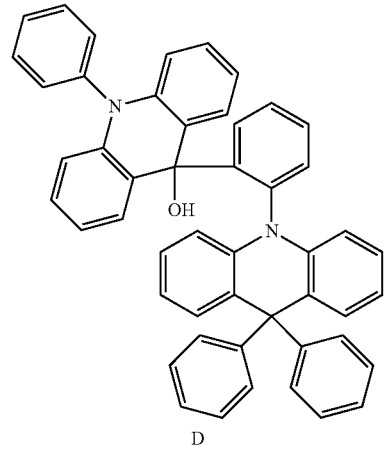

Under an argon (Ar) atmosphere, 7 mL of a hexane solution containing 1.6 mol/L n-BuLi was added to 100 mL of a THF solution containing 4.0 g of Compound C cooled to about −78° C. and the mixture was stirred for about 1 hour. 50 mL of THF solution containing 5.7 g of 10-phenylacridone was added thereto dropwise for about 1 hour under cooling conditions, and then the resultant was stirred at ambient temperature for about 6 hours. An aqueous ammonium oxide solution was added to the obtained reaction solution and the resultant was concentrated under vacuum. The residue was dissolved in methylene chloride and then purified by column chromatography to obtain 5.2 g (yield 64%) of Compound D as a white powder.

(Synthesis of Compound 12)

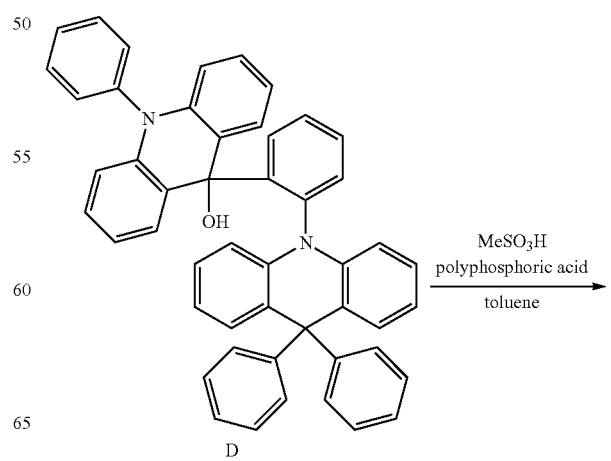

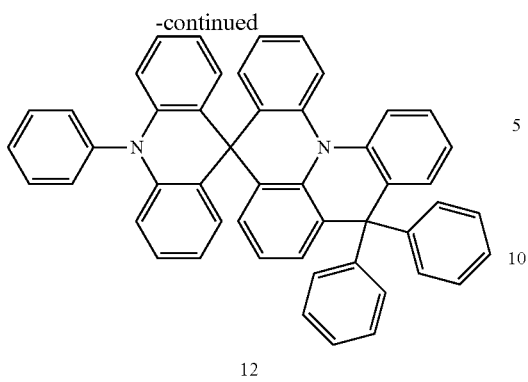

12

5.0 g of Compound D in toluene was heated in the presence of polyphosphoric acid at about 60° C. for about 6 hours. After cooling, the reactant was extracted with water-dichloromethane, and organic layer was concentrated under reduced pressure. The residue was purified by column chromatography to obtain 4.6 g (yield 93%) of Compound 12 as a white powder. The molecular weight of Compound 12 measured by FAB-MS was 662. From the results, the compound thus synthesized was identified as Compound 12.

4. Synthesis of Compound 19

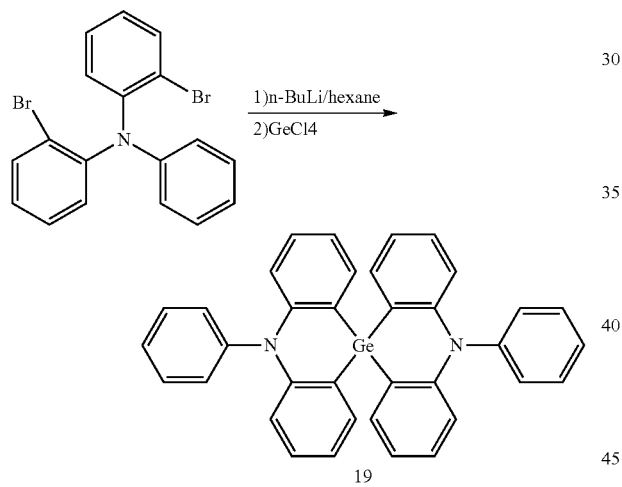

19

Under an argon atmosphere, 9.34 mL of a hexane solution containing 1.6 mol/L n-BuLi was added to 100 mL of a THF solution containing 3.0 g of 2,2'-dibromo-triphenylamine cooled to about −78° C. and the mixture was stirred for about 1 hour. 0.5 mL of germanium chloride was added thereto dropwise for about 1 hour under cooling conditions, and then the resultant was heated to ambient temperature and then stirred for about 24 hours. Ethanol and an aqueous ammonium chloride solution were added to the obtained reaction solution to stop the reaction and the resultant was concentrated under reduced pressure. The residue was dissolved in dichloromethane and then purified by column chromatography to obtain 10.63 g (yield 30%) of Compound 19 as a white powder.

Device Manufacturing Examples

Organic electroluminescence devices of Examples 1 to 4 were manufactured by using Compounds 1, 2, 12 and 19 as electron blocking layer materials.

[Example Compounds]

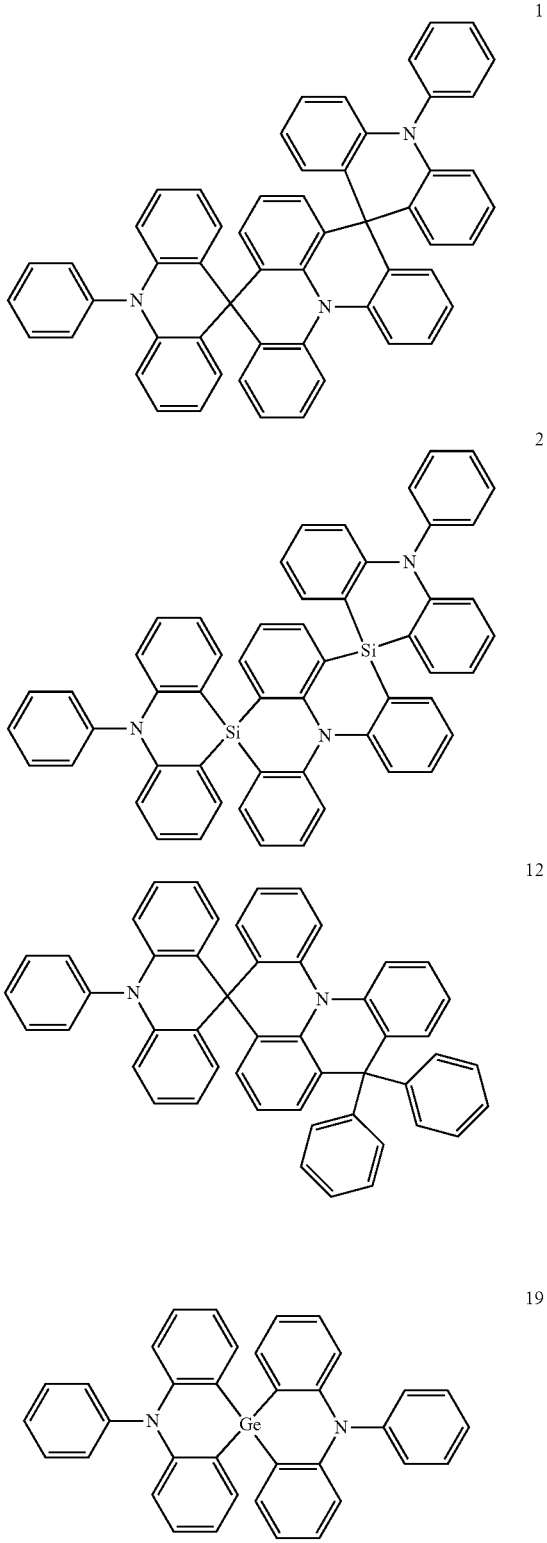

Organic electroluminescent devices of Comparative Examples 1 to 4 were manufactured by using the following Comparative Compounds c1 to c4 as electron blocking layer materials.

[Comparative Compounds]

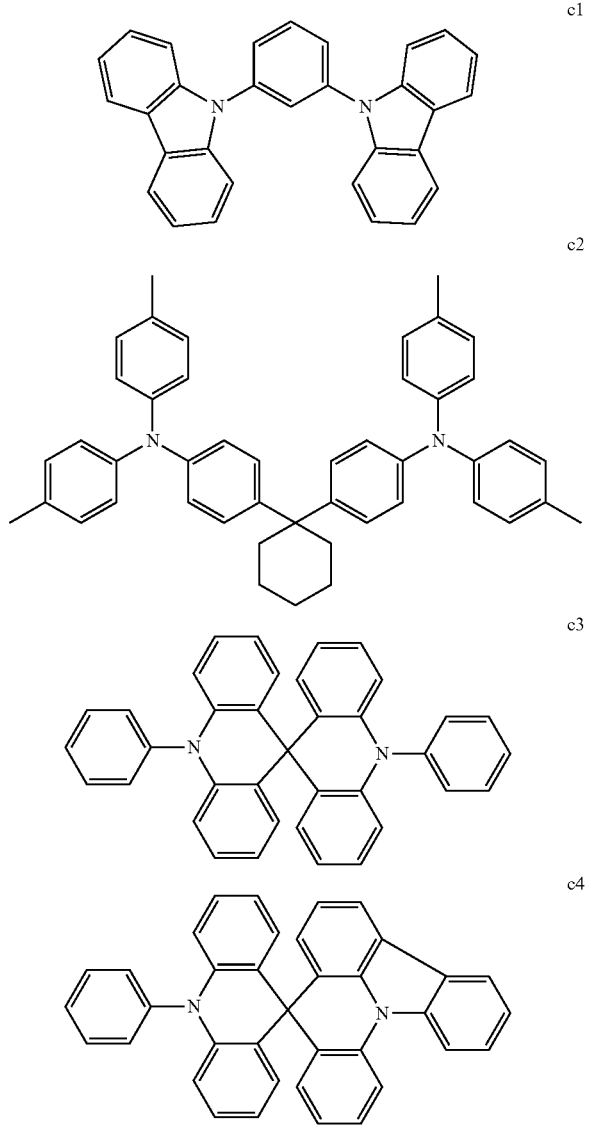

The organic electroluminescence devices according to Examples 1 to 4 and Comparative Examples 1 to 4 were manufactured by forming a first electrode using ITO to a thickness of about 150 nm, a hole injection layer using 1,4,5,8,9,11-hexaazatriphenylenehexacarbonitrile (HAT-CN) to a thickness of about 10 nm, a hole transport layer using N,N'-di(naphthalen-1-yl)-N,N'-diphenyl-benzidine (NPB) to a thickness of about 80 nm, an electron blocking layer using the Example Compounds or the Comparative Compounds to a thickness of about 5 nm, an emission layer using bis[2-(diphenylphosphino)phenyl]ether oxide (DPEPO) doped with 18% 10-phenyl-10H,10'H-spiro[acridine-9,9'-anthracen]-10'-one (ACRSA) to a thickness of about 20 nm, a hole blocking layer using DPEPO to a thickness of about 10 nm, an electron transport layer using 1,3,5-tris(1-phenyl-1H-benzimidazol-2-yl) benzene (TPBi) to a thickness of about 30 nm, an electron injection layer using lithium fluoride (LiF) to a thickness of about 0.5 nm, and a second electrode using Al to a thickness of about 100 nm. Each layer was formed by a deposition method in a vacuum atmosphere.

The driving voltage and external quantum efficiency of the manufactured organic electroluminescence devices were evaluated. The driving voltage of each Example and Comparative Example was a measured value at a current density of 10 mA/cm².

TABLE 1

| Device manufacturing example | Electron blocking layer material | Driving voltage (V) | External quantum efficiency (%) |
| --- | --- | --- | --- |
| Example 1 | Example Compound 1 | 5.9 | 16.5 |
| Example 2 | Example Compound 2 | 6.1 | 16.7 |
| Example 3 | Example Compound 12 | 6.1 | 16.0 |
| Example 4 | Example Compound 19 | 6.0 | 17.0 |
| Comparative Example 1 | Comparative Compound c1 | 6.6 | 15.0 |
| Comparative Example 2 | Comparative Compound c2 | 6.2 | 12.0 |
| Comparative Example 3 | Comparative Compound c3 | 6.0 | 14.5 |
| Comparative Example 4 | Comparative Compound c4 | 6.1 | 12.2 |

Referring to the results in Table 1, it may be seen that the organic electroluminescence device including the polycyclic compound of Examples 1 to 4 attained high emission efficiency and a low driving voltage.

Table 2 shows the calculated HOMO energy and the lowest triplet excitation energy (T1) of Example Compounds and Comparative Compounds. The HOMO energy and the lowest triplet excitation energy were calculated using TD-B3LYP/631-G (d) by the theoretical chemistry simulation software Gaussian09.

TABLE 2

| Compound | HOMO energy (eV) | Lowest triplet excitation energy (eV) |
| --- | --- | --- |
| Example Compound 1 | −4.85 | 3.18 |
| Example Compound 2 | −5.04 | 3.22 |
| Example Compound 12 | −4.96 | 3.16 |
| Example Compound 19 | −4.99 | 3.27 |
| Comparative Compound c1 | −5.45 | 3.18 |
| Comparative Compound c2 | −4.70 | 3.10 |
| Comparative Compound c3 | −4.86 | 3.15 |
| Comparative Compound c4 | −5.05 | 3.08 |

Comparing the Example Compounds 1 to 4 and Comparative Compounds c1 to c4, the polycyclic compound of the Examples had a high level of the lowest triplet excitation energy and a high level of the HOMO energy. For example, use of the polycyclic compound according to an embodiment as a hole transport material in the hole transport region adjacent to the emission layer may attain a high hole transport property and inhibits the diffusion of triplet excitons generated in the emission layer into the hole transport region, thereby securing a low driving voltage and high emission efficiency of an organic electroluminescence device.

Comparative Compound c1 had a HOMO energy lower when compared with those of Example Compounds 1 to 4, and therefore may have a decreased hole transport property. Thus, the organic electroluminescence device of Comparative Example 1 had a higher driving voltage when compared with those of Examples 1 to 4, and had low emission efficiency.

Comparative Compounds c2 and c3 had the lowest triplet excitation energy lower when compared with those of Example Compounds 1 to 4, and therefore had a decreased effect of inhibiting the diffusion of triplet excitons generated in the emission layer into the hole transport region. Thus, the organic electroluminescence devices of Comparative Examples 2 and 3 had a lower emission efficiency when compared with those of Examples 1 to 4.

Comparative Compound c4 had the lowest triplet excitation energy and the HOMO energy, both of which were lower when compared with those of Example Compounds 1 to 4, and therefore had a decreased hole transport property and also decreased effect of inhibiting the diffusion of triplet excitons generated in the emission layer into the hole transport region. Thus, the organic electroluminescence device of Comparative Example 4 had a lower emission efficiency when compared with those of Examples 1 to 4.

The embodiments may provide a polycyclic compound used in an organic electroluminescence device with high emission efficiency.

The embodiments may provide an organic electroluminescence device with high emission efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A polycyclic compound represented by the following Formula 1:

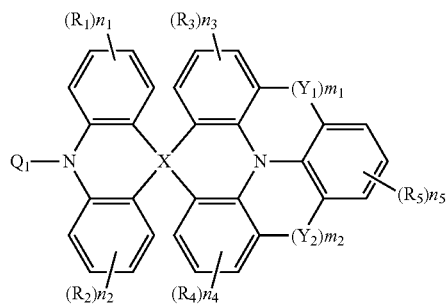

[Formula 1]

wherein, in Formula 1,

X is C, Si, Ge, or Sn, $Y_1$ and $Y_2$ are each independently O, S, $CR_6R_7$, $SiR_8R_9$, $GeR_{10}R_{11}$, or $SnR_{12}R_{13}$, $R_1$ to $R_{13}$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group, $R_1$ to $R_{13}$ are separate or form a ring by combining adjacent groups with each other, $Q_1$ is a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $n_1$ and $n_2$ are each independently an integer of 0 to 4, $n_3$ to $n_5$ are each independently an integer of 0 to 3, $m_1$ and $m_2$ are each independently 0 or 1, and when X is C or Si, at least one of $m_1$ or $m_2$ is 1.

2. The polycyclic compound as claimed in claim 1, wherein $Y_1$ and $Y_2$ are each independently represented by the following Formula 2:

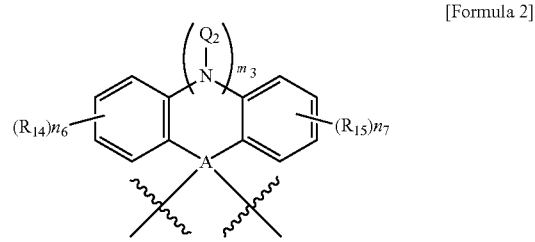

[Formula 2]

wherein, in Formula 2,

A is C, Si, Ge, or Sn, $R_{14}$ and $R_{15}$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group, $R_{14}$ and $R_{15}$ are separate or form a ring by combining adjacent groups with each other, $Q_2$ is a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $n_6$ and $n_7$ are each independently an integer of 0 to 4, $m_3$ is 0 or 1, and

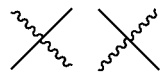

represent bonding sites of $Y_1$ and $Y_2$ in Formula 1.

3. The polycyclic compound as claimed in claim 1, wherein the polycyclic compound represented by Formula 1 is represented by any one of the following Formulae 3-1 to 3-6:

[Formula 3-1]

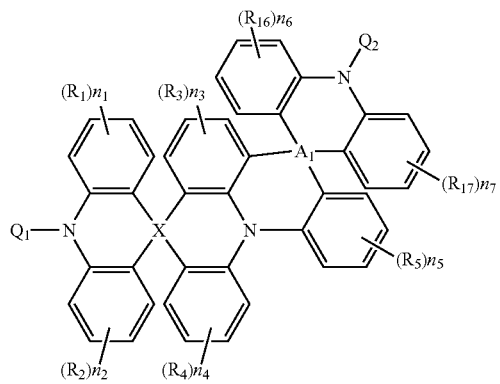

[Formula 3-2]

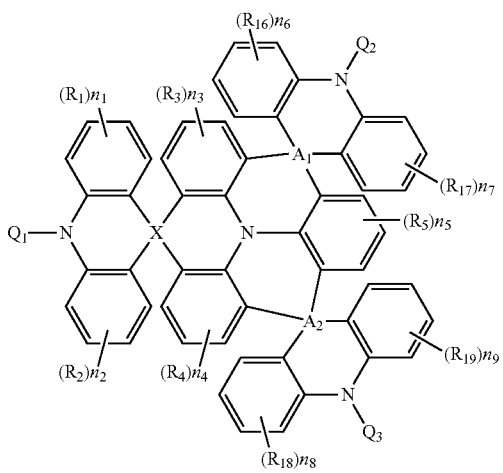

[Formula 3-3]

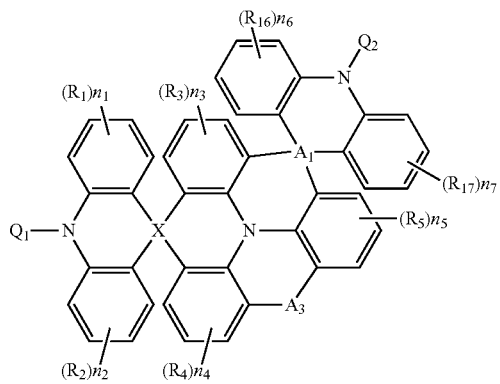

[Formula 3-4]

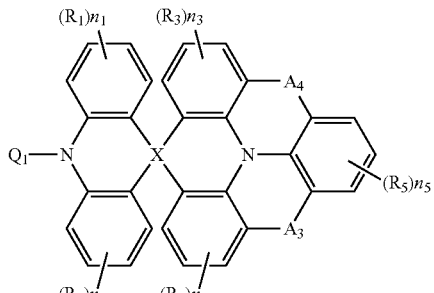

[Formula 3-5]

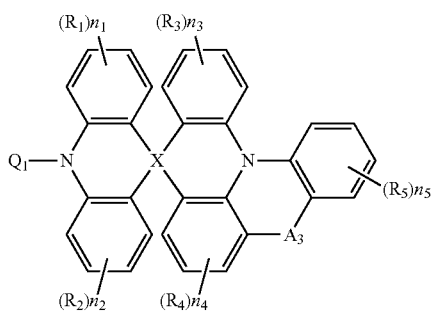

[Formula 3-6]

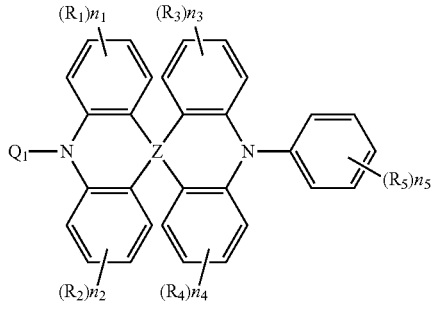

wherein, in Formulae 3-1 to 3-6, $A_1$ and $A_2$ are each independently C, Si, Ge, or Sn, $A_3$ and $A_4$ are each independently O, S, $CR_{20}R_{21}$, $SiR_{22}R_{23}$, $GeR_{24}R_{25}$, or $SnR_{26}R_{27}$, $R_{16}$ to $R_{27}$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group, $R_{16}$ to $R_{27}$ are separate or form a ring by combining adjacent groups with each other, $Q_2$ and $Q_3$ are each independently a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, Z is Ge or Sn, $n_6$ to $n_9$ are each independently an integer of 0 to 4, and X, $Q_1$, $R_1$ to $R_5$, and $n_1$ to $n_5$ are defined the same as those of Formula 1.

4. The polycyclic compound as claimed in claim 3, wherein $R_{20}$ to $R_{27}$ are each independently a hydrogen atom, a substituted or unsubstituted alkyl group having 1 to 10 carbon atoms, or a substituted or unsubstituted aryl group having 6 to 15 ring carbon atoms.

5. The polycyclic compound as claimed in claim 3, wherein $Q_1$ to $Q_3$ are each independently a substituted or unsubstituted alkyl group having 1 to 10 carbon atoms or a substituted or unsubstituted aryl group having 6 to 15 ring carbon atoms.

6. The polycyclic compound as claimed in claim 1, wherein X is C, Si, or Ge.

7. The polycyclic compound as claimed in claim 1, wherein $Y_1$ and $Y_2$ are each independently $CR_6R_7$ or $SiR_8R_9$.

8. The polycyclic compound as claimed in claim 1, wherein the polycyclic compound represented by Formula 1 is a compound of the following Compound Group 1:

[Compound Group 1]

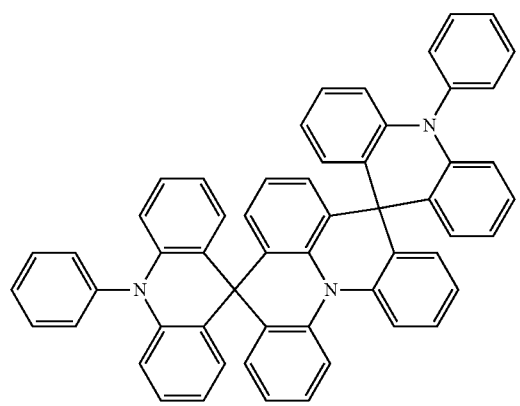

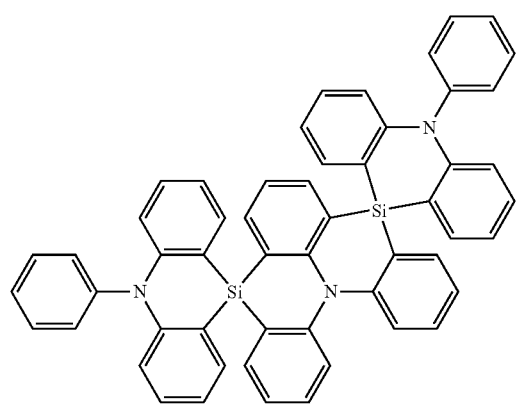

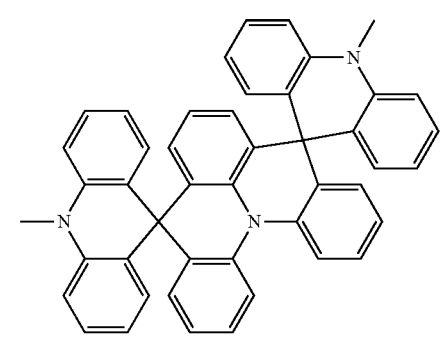

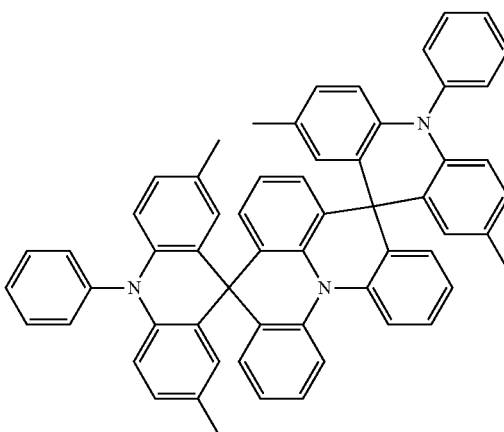

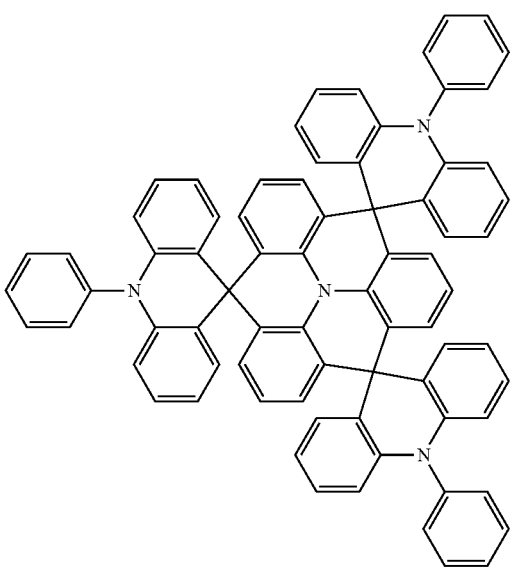

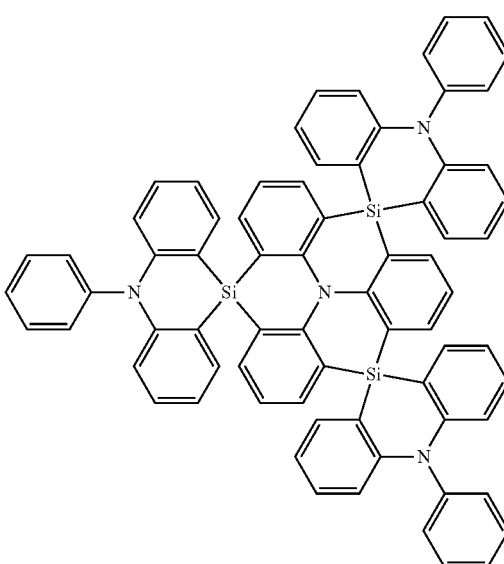

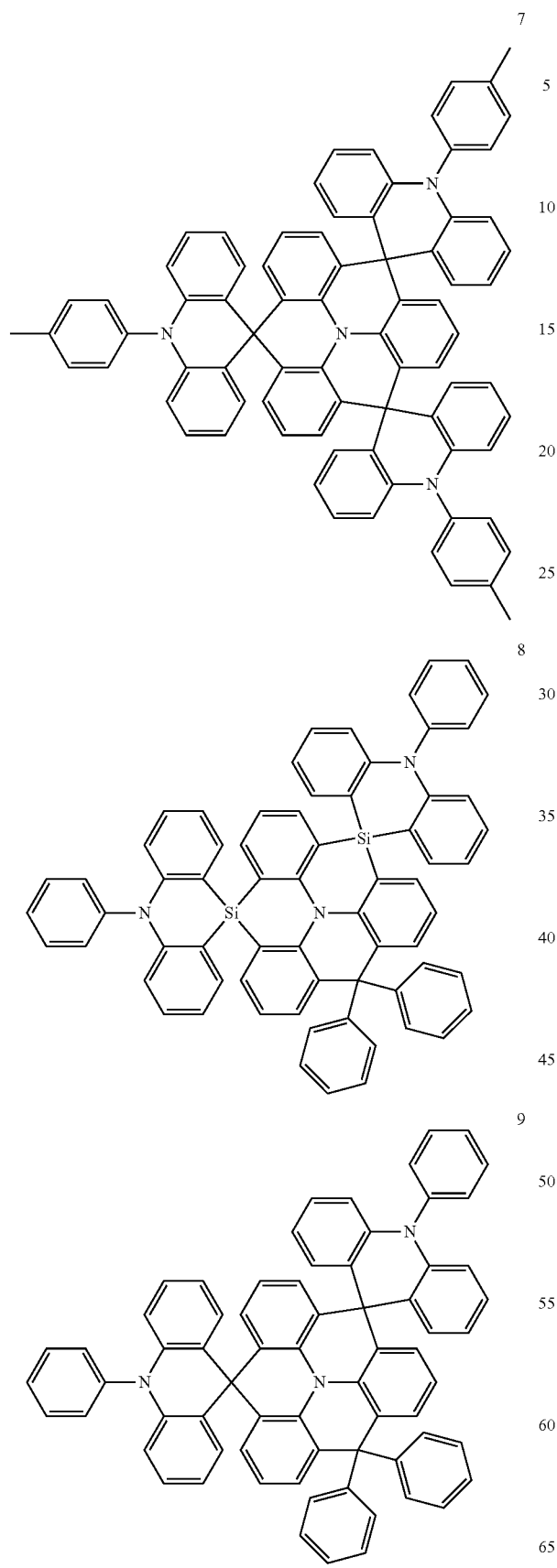
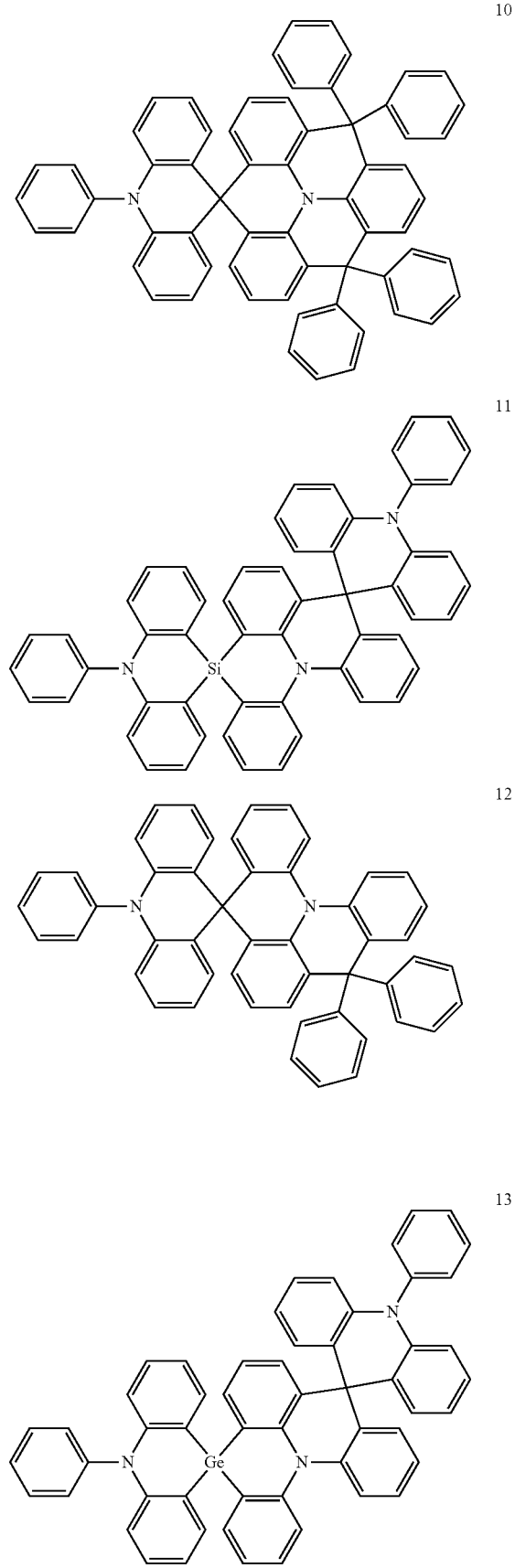

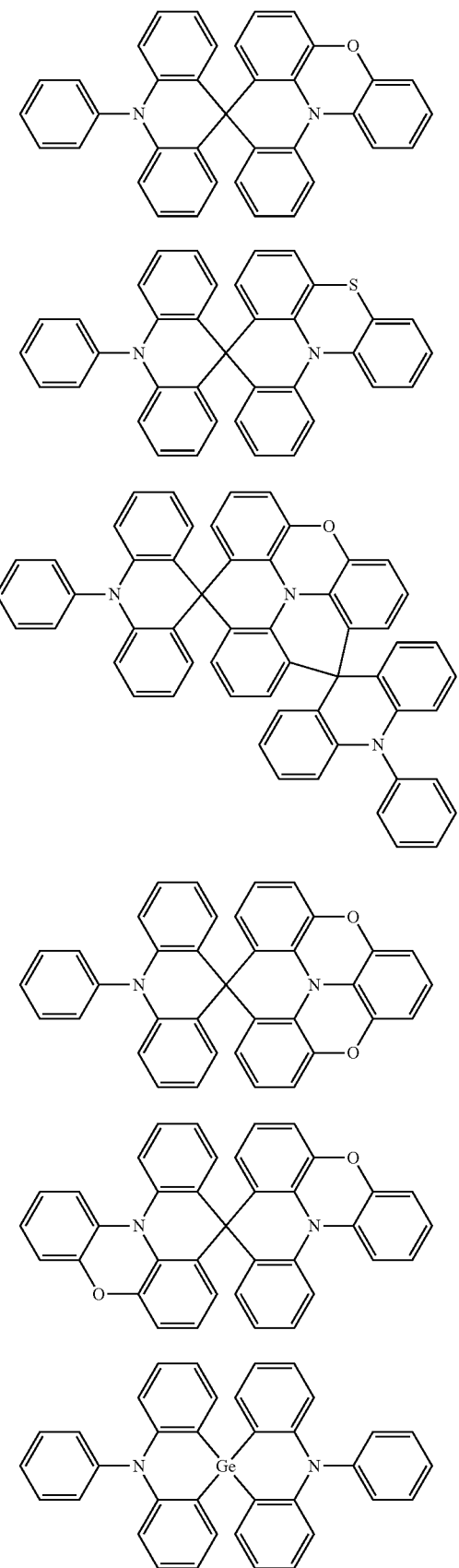

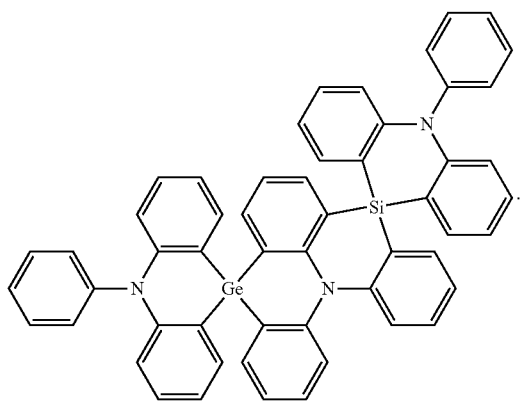

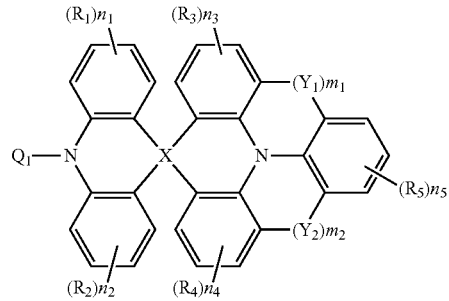

9. An organic electroluminescence device, comprising:
a first electrode;
a hole transport region on the first electrode;
an emission layer on the hole transport region;
an electron transport region on the emission layer; and
a second electrode on the electron transport region,
wherein the hole transport region includes a polycyclic compound represented by the following Formula 1:

[Formula 1]

wherein, in Formula 1,
X is C, Si, Ge, or Sn,
$Y_1$ and $Y_2$ are each independently O, S, $CR_6R_7$, $SiR_8R_9$, $GeR_{10}R_{11}$, or $SnR_{12}R_{13}$,
$R_1$ to $R_{13}$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group,
$R_1$ to $R_{13}$ are separate or form a ring by combining adjacent groups with each other,
$Q_1$ is a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
$n_1$ and $n_2$ are each independently an integer of 0 to 4,
$n_3$ to $n_5$ are each independently an integer of 0 to 3,
$m_1$ and $m_2$ are each independently 0 or 1, and
when X is C or Si, at least one of $m_1$ or $m_2$ is 1.

10. The organic electroluminescence device as claimed in claim 9, wherein:
the hole transport region includes:
a hole injection layer on the first electrode; and
a hole transport layer on the hole injection layer, and
the hole transport layer includes the polycyclic compound represented by Formula 1.

11. The organic electroluminescence device as claimed in claim 9, wherein:
the hole transport region includes:
a hole injection layer on the first electrode;
a hole transport layer on the hole injection layer; and
an electron blocking layer on the hole transport layer, and
the electron blocking layer includes the polycyclic compound represented by Formula 1.

12. The organic electroluminescence device as claimed in claim 9, wherein $Y_1$ and $Y_2$ are each independently represented by the following Formula 2:

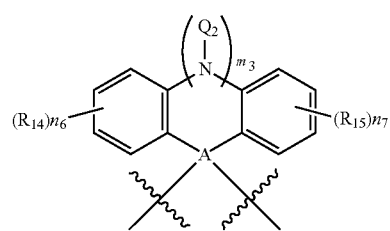

[Formula 2]

wherein, in Formula 2,

A is C, Si, Ge, or Sn, $R_{14}$ and $R_{15}$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group, $R_{14}$ and $R_{15}$ are separate or form a ring by combining adjacent groups with each other, $Q_2$ is a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $n_6$ and $n_7$ are each independently an integer of 0 to 4, $m_3$ is 0 or 1, and

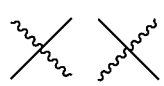

represent bonding sites of $Y_1$ and $Y_2$ in Formula 1.

13. The organic electroluminescence device as claimed in claim 9, wherein the polycyclic compound represented by Formula 1 is represented by any one of the following Formulae 3-1 to 3-6:

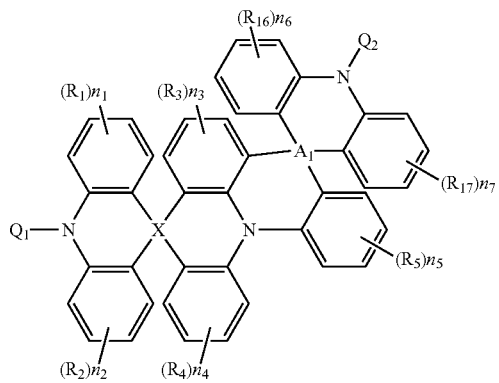

[Formula 3-1]

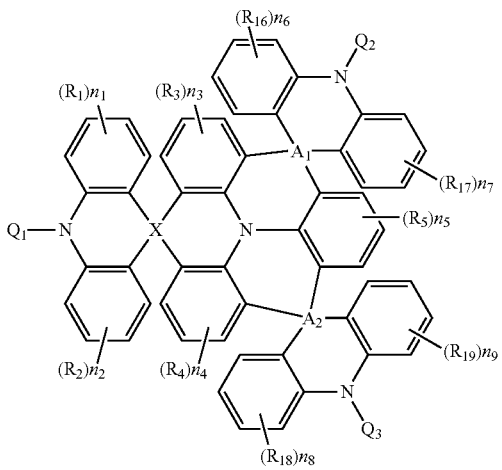

[Formula 3-2]

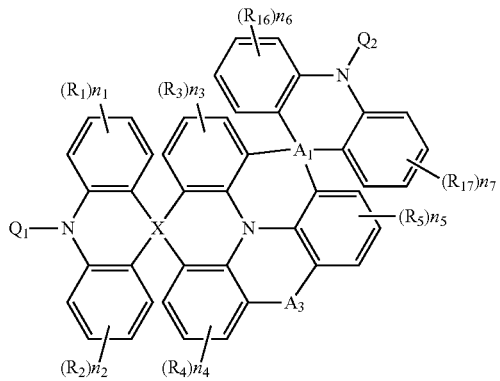

[Formula 3-3]

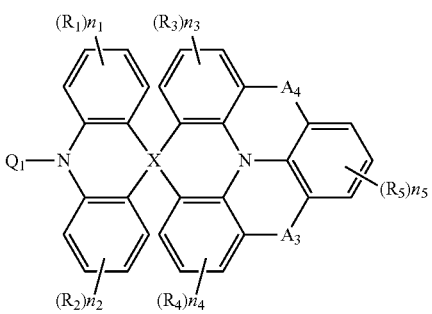

[Formula 3-4]

-continued

[Formula 3-5]

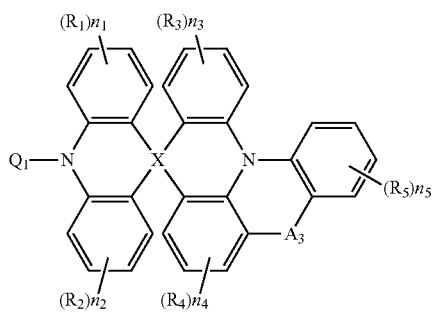

[Formula 3-6]

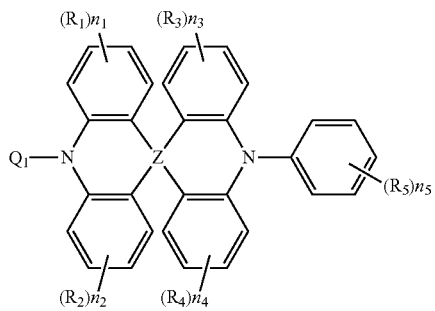

wherein, in Formulae 3-1 to 3-6,
$A_1$ and $A_2$ are each independently C, Si, Ge, or Sn,
$A_3$ and $A_4$ are each independently O, S, $CR_{20}R_{21}$, $SiR_{22}R_{23}$, $GeR_{24}R_{25}$, or $SnR_{26}R_{27}$,
$R_{16}$ to $R_{27}$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, a substituted or unsubstituted cyano group, or a substituted or unsubstituted silyl group,
$R_{16}$ to $R_{27}$ are separate or form a ring by combining adjacent groups with each other,
$Q_2$ and $Q_3$ are each independently a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
Z is Ge or Sn,
$n_6$ to $n_9$ are each independently an integer of 0 to 4, and
X, $Q_1$, $R_1$ to $R_5$, and $n_1$ to $n_5$ are defined the same as those of Formula 1.

14. The organic electroluminescence device as claimed in claim 13, wherein $R_{20}$ to $R_{27}$ are each independently a hydrogen atom, a substituted or unsubstituted alkyl group having 1 to 10 carbon atoms, or a substituted or unsubstituted aryl group having 6 to 15 ring carbon atoms.

15. The organic electroluminescence device as claimed in claim 13, wherein $Q_1$ to $Q_3$ are each independently a substituted or unsubstituted alkyl group having 1 to 10 carbon atoms or a substituted or unsubstituted aryl group having 6 to 15 ring carbon atoms.

16. The organic electroluminescence device as claimed in claim 9, wherein X is C, Si, or Ge.

17. The organic electroluminescence device as claimed in claim 9, wherein $Y_1$ and $Y_2$ are each independently $CR_6R_7$ or $SiR_8R_9$.

18. The organic electroluminescence device as claimed in claim 9, wherein the polycyclic compound represented by Formula 1 is a compound of the following Compound Group 1:

[Compound Group 1]

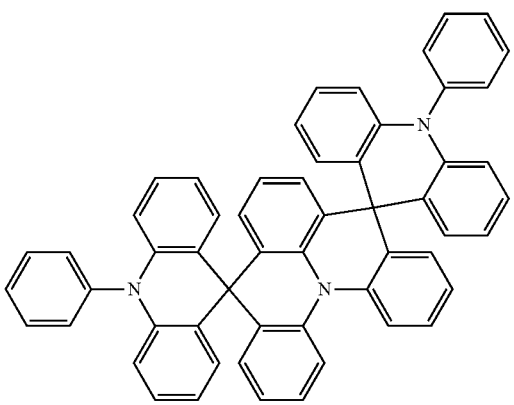

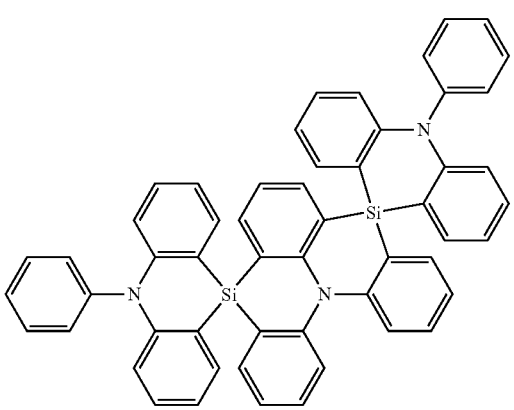

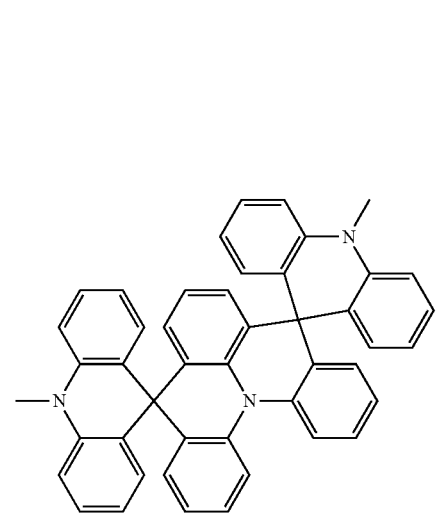

4
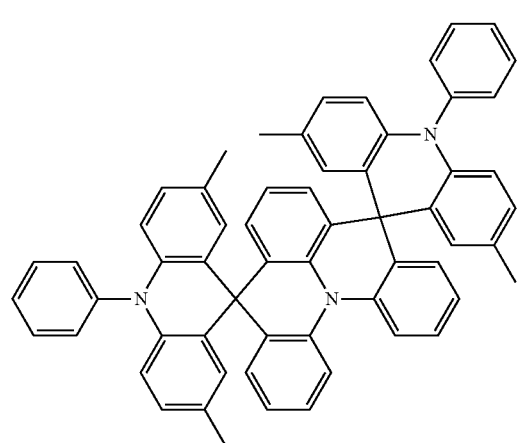
5
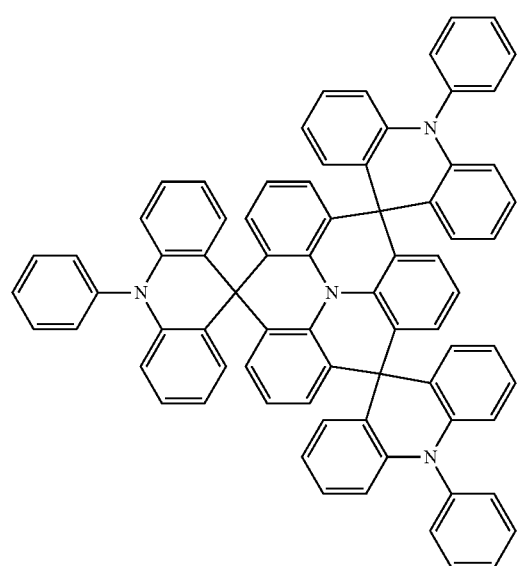
6
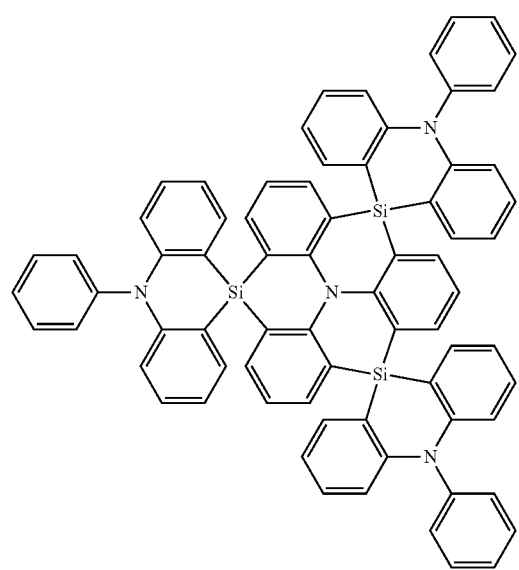
7
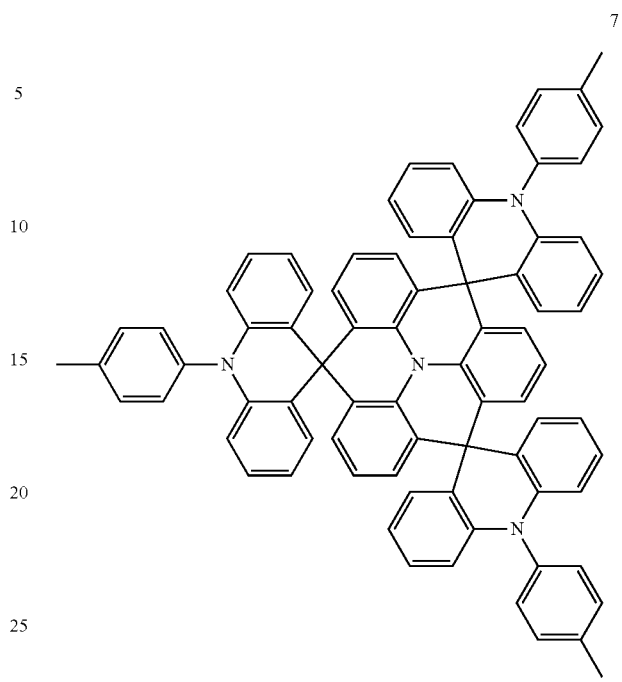
8
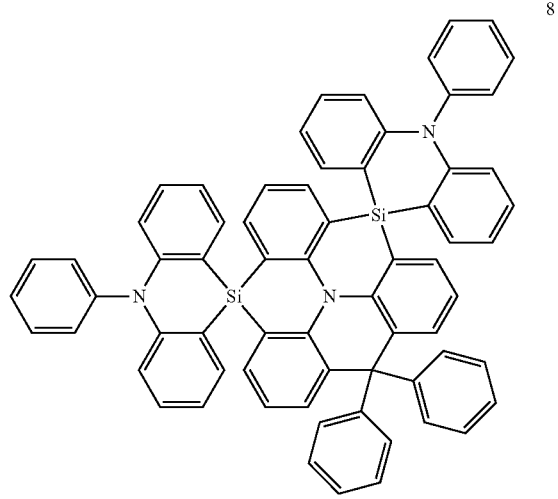
9
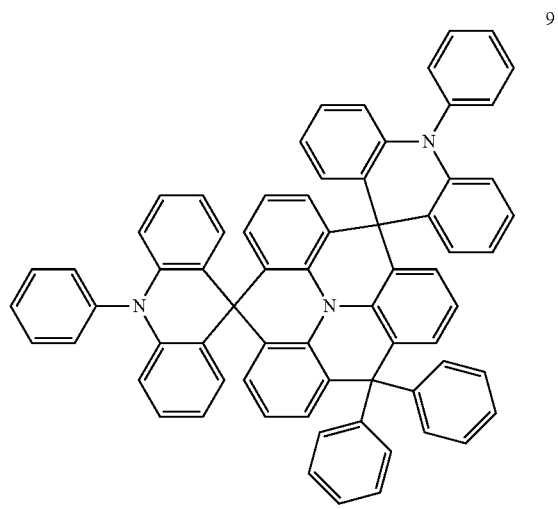

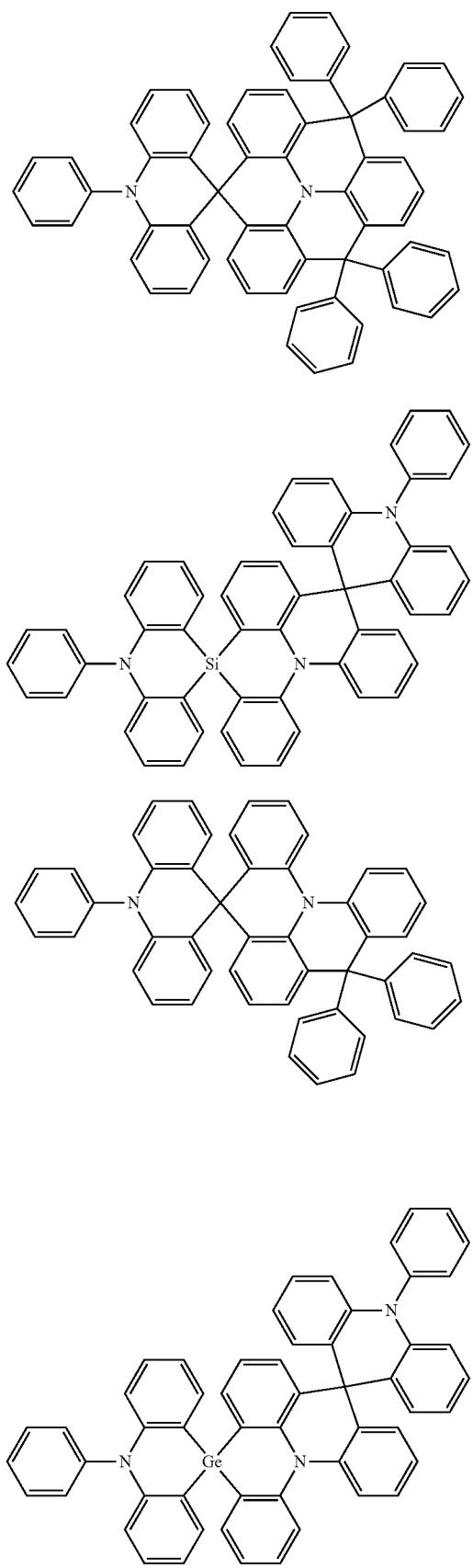
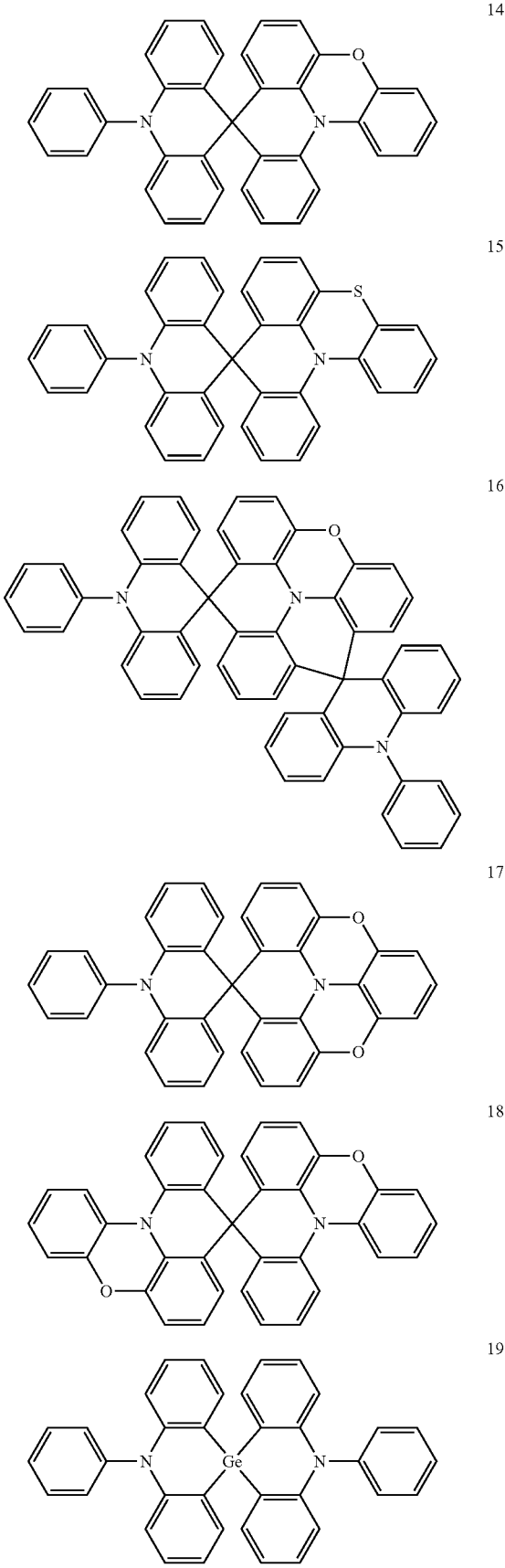

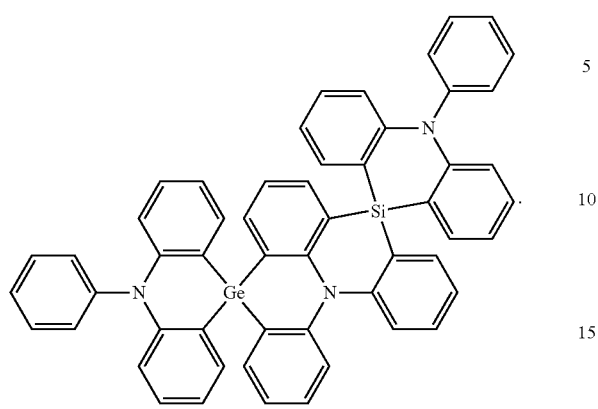
19. The organic electroluminescence device as claimed in claim 9, wherein the polycyclic compound represented by Formula 1 is a thermally activated delayed fluorescence (TADF) luminescence material or a phosphorescence luminescence material.
* * * * *